United States Patent [19]
Brieaddy

[11] Patent Number: 5,910,494
[45] Date of Patent: Jun. 8, 1999

[54] HYPOLIPIDEMIC 1,4-BENZOTHIAZEPINE-1,1-DIOXIDES

[75] Inventor: Lawrence Edward Brieaddy, Raleigh, N.C.

[73] Assignee: Glaxo Wellcome Inc., Research Triangle Park, N.C.

[21] Appl. No.: 08/793,040

[22] PCT Filed: Aug. 9, 1995

[86] PCT No.: PCT/GB95/01884

§ 371 Date: Feb. 7, 1997

§ 102(e) Date: Feb. 7, 1997

[87] PCT Pub. No.: WO96/05188

PCT Pub. Date: Feb. 22, 1996

[51] Int. Cl.⁶ ............ C07D 281/10; C07D 417/04; C07D 513/04; A61K 31/55
[52] U.S. Cl. .......... 514/211; 514/221; 540/546; 540/552; 540/595
[58] Field of Search .................. 540/546, 552, 540/595; 514/211, 221

[56] References Cited

U.S. PATENT DOCUMENTS

| | | | |
|---|---|---|---|
| 3,362,962 | 1/1968 | Reeder et al. | 260/294.8 |
| 3,503,985 | 3/1970 | Reeder et al. | 260/294.8 |
| 3,523,974 | 8/1970 | Reeder et al. | 260/591 |
| 3,530,139 | 9/1970 | Reeder et al. | 260/294.8 |
| 3,631,089 | 12/1971 | Reeder et al. | 260/455 |
| 4,564,612 | 1/1986 | Sugihara et al. | 514/211 |
| 5,276,025 | 1/1994 | Baldwin et al. | 514/211 |

FOREIGN PATENT DOCUMENTS

| | | |
|---|---|---|
| WO 92/21668 | 12/1992 | WIPO . |
| WO A93 16055 | 8/1993 | WIPO . |
| WO A94 18183 | 8/1994 | WIPO . |
| WO A94 18184 | 8/1994 | WIPO . |
| WO 96/08484 | 3/1996 | WIPO . |
| WO 96/16051 | 5/1996 | WIPO . |

OTHER PUBLICATIONS

Anonymous, "Pharmaceutical Compounds", Research Disclosure, vol. 354, pp.691–693, Emsworth, GB (Oct. 1993).
Sternbach et al. "A New type of 1,4–benzothiazepine derivatives," J. Org. Chem, 30(8), 2812–2818 (1965).
Nair et al., "Synthesis & Reactions of Benz[1,4]thiazepines Derivatives," Indian J. Chem., 7(9), 862–865 (1969).
Grundy, "Cholesterol and Coronary Heart Disease", J. Amer. Med. Assn, 256(20), 2849–2859 (1986).
Sugano et al., "Suppression of Atherosclerosis in Cholesterol–Fed Rabbits by Diltiazem Injection," Arteriosclerosis, 6(2), 237–241 (1986).
Szabo et al. Synthesis and Spectroscopic Investigation of 1,4–Benzothiazepine Derivatives, Chemical Abstracts, 108:221680x (1988).
Szabo et al. "Saturated Heterocycles. Part 116. Synthesis and Spectroscopic Investigations of 1,4–Benzothiazepine Derivatives," Heterocycles, 108:5984g (1988).

*Primary Examiner*—Allen J. Robinson
*Assistant Examiner*—Sabiha N. Qazi
*Attorney, Agent, or Firm*—Lorie Ann Morgan; Robert T. Hrubiec

[57] ABSTRACT

The invention is concerned with novel hypolipidemic compounds of formula (I), with processes and novel intermedites for their preparation, pharmaceutical compositions containing them and with their use in medicine, particularly in the prophylaxis and treatment of hyperlipidemic conditions, such as atherosclerosis.

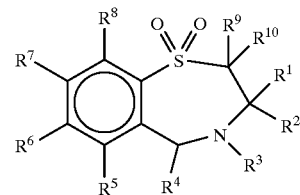

28 Claims, No Drawings

HYPOLIPIDEMIC 1,4-BENZOTHIAZEPINE-1,1-DIOXIDES

This application has been filed under 35 USC 371 as a national stage application of PCT/GB95/01884, filed Aug. 9, 1995.

The present invention is concerned with new hypolipidemic compounds, with processes and novel intermediates for their preparation, with pharmaceutical compositions containing them and with their use in medicine, particularly in the prophylaxis and treatment of hyperlipidemic conditions, such as atherosclerosis.

Hyperlipidemic conditions are often associated with elevated plasma concentrations of low density lipoprotein (LDL) cholesterol and very low density lipoprotein (VLDL) cholesterol. Such concentrations can be reduced by decreasing the absorption of bile acids from the intestine. One method by which this may be achieved is to inhibit the bile acid active uptake system in the terminal ileum. Such inhibition stimulates the conversion of cholesterol to bile acid by the liver and the resulting increase in demand for cholesterol produces a corresponding increase in the rate of clearance of LDL and VLDL cholesterol from the blood plasma or serum.

There has now been identified a novel class of heterocyclic compounds which reduce the plasma or serum concentrations of LDL and VLDL cholesterol and in consequence are particularly useful as hypolipidemic agents. By decreasing the concentrations of cholesterol and cholesterol ester in the plasma, the compounds of the present invention retard the build-up of atherosclerotic lesions and reduce the incidence of coronary heart disease-related events. The latter are defined as cardiac events associated with increased concentrations of cholesterol and cholesterol ester in the plasma or serum.

For the purposes of this specification, a hyperlipidemic condition is defined as any condition wherein the total cholesterol concentration (LDL+VLDL) in the plasma or serum is greater than 240 mg/dL (6.21 mmol/L) (J. Amer. Med. Assn. 256, 20, 2849–2858 (1986)).

International Patent Application No. WO 93/16055 describes compounds of formula (O)

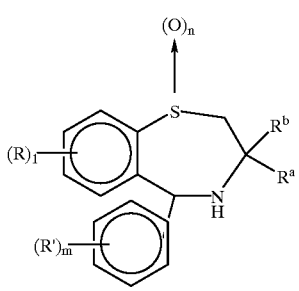

(O)

wherein
1 is an integer of from 0 to 4;
m is an integer of from 0 to 5;
n is an integer of from 0 to 2;
R and R' are atoms or groups independently selected from halogen, nitro, phenylalkoxy,
$C_{1-4}$ alkoxy, $C_{1-6}$ alky, and $—O(CH_2)_pSO_3R''$ wherein p is an integer of from 1 to 4 and
R" is hydrogen or $C_{1-6}$ alky, wherein said phenylalkoxy, alkoxy and all groups are optionally substituted by one or more halogen atoms;

$R^a$ is a $C_{1-6}$ straight, that is, unbranched, alkyl group; and
$R^b$ is a $C_{2-6}$ straight, that is, unbranched, alkyl group; and salts, solvates and physiologically functional derivatives thereof, as being useful as hypolipidemic agents.

We have now discovered a group of compounds which have greater hypolipidemic activity in vivo than those specifically disclosed in International Patent Application No. WO 93/16055.

Accordingly the present invention provides compounds of the formula (I):

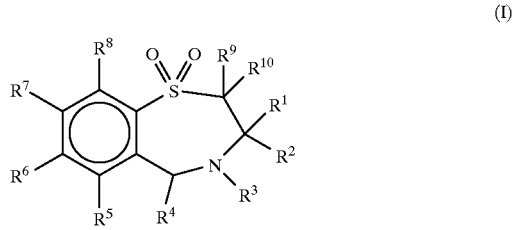

(I)

wherein $R^1$ is a straight chained $C_{1-6}$ alkyl group; $R^2$ is a straight chained $C_{1-6}$ alkyl group; $R^3$ is hydrogen or a group $OR^{11}$ in which $R^{11}$ is hydrogen, optionally substituted $C_{1-6}$ alkyl or a $C_{1-6}$ alkylcarbonyl group; $R^4$ is pyridyl or optionally substituted phenyl; $R^5$, $R^6$, $R^7$ and $R^8$ are the same or different and each is selected from hydrogen, halogen, cyano, $R^{15}$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, $OCN$, $SCN$, $NHCN$, $CH_2OR^{15}$, $CHO$, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH=CHR^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein p is an integer from 1–4, n is an integer from 0–3 and, $R^{12}$, $R^{13}$, $R^{14}$ and $R^{15}$ are independently selected from hydrogen and optionally substituted $C_{1-6}$ alkyl; or $R^6$ and $R^7$ are linked to form a group

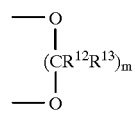

wherein $R^{12}$ and $R^{13}$ are as hereinbefore defined and m is 1 or 2; and $R^9$ and $R^{10}$ are the same or different and each is hydrogen or $C_{1-6}$ alkyl; and salts, solvates or a physiologically functional derivatives thereof, with the proviso that when $R^3$ is hydrogen either $R^7$ is not hydrogen or at least two of $R^5$, $R^6$, $R^7$ and $R^8$ are not hydrogen; and salts, solvates, and physiologically functional derivatives thereof.

When $R^4$ is a substituted phenyl group, there may be one to five, preferably one or two substituents which are the same or different and are each selected from halogen, hydroxy, nitro, phenyl-$C_{1-6}$ alkoxy, $C_{1-6}$ alkoxy, optionally substituted $C_{1-6}$ alkyl, $S(O)_nR^{15}$, $CO_2R^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein $R^{12}$ to $R^{15}$, n and p are as hereinbefore defined.

According to a further aspect, the invention provides compounds of formula (I) wherein:
$R^1$ and $R^2$ are straight chained $C_{1-6}$ alkyl;
$R^3$ is hydrogen or hydroxy;
$W^4$ is unsubstitued pheryl;
$R^5$ is hydrogen;

3

$R^9$ and $R^{10}$ are both hydrogen; and either $R^7$ is selected from halogen, hydroxy, $C_{1-6}$ alkoxy, optionally substituted $C_{1-6}$ alkyl, —S(O)$_n$R$^{15}$, —OC(O)R$^{15}$, and —CH$_2$OR$^{15}$ wherein R$^{15}$ is hydrogen or $C_{1-6}$ alkyl; and $R^6$ and $R^8$ are independently selected from hydrogen and those groups listed in the definition of $R^7$; or $R^8$ is hydrogen and $R^6$ and $R^7$ are linked to form a group —O—(CH$_2$)$_m$—O— wherein m is 1 or 2;

and salts, solvates, and physiologically functional derivatives thereof

Of the compounds of formula (I), those in which $R^8$ is hydrogen and $R^6$ and $R^7$ are both $C_{1-6}$ alkoxy, more particularly both methoxy, are preferred.

Preferred embodiments of the compounds of formula (I) include compounds of the formula (II), (III), (IV) or (IVa)

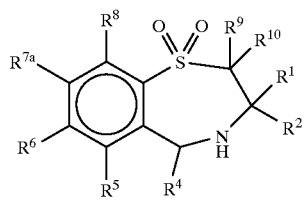

(II)

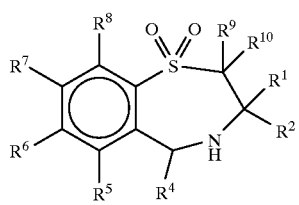

(III)

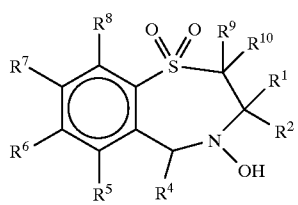

(IV)

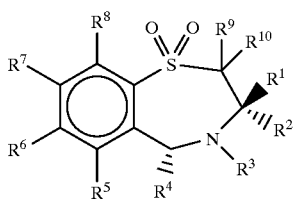

(IVa)

wherein $R^1$ to $R^{10}$ are as hereinbefore defined and $R^{7a}$ is selected from halogen, cyano, $R^{15}$-acetylide, OR$^{15}$, optionally substituted $C_{1-6}$ alkyl, COR$^{15}$, CH(OH)R$^{15}$, S(O)$_n$R$^{15}$, P(O)(OR$^{15}$)$_2$, OCOR$^{15}$, OCF$_3$, OCN, SCN, HNCN, CH$_2$OR$^{15}$, CHO, (CH$_2$)$_p$CN, CONR$^{12}$R$^{13}$, (CH$_2$)$_p$CO$_2$R$^{15}$, (CH$_2$)$_p$NR$^{12}$R$^{13}$, CO$_2$R$^{15}$, NHCOCF$_3$, NHSO$_2$R$^{15}$, OCH$_2$OR$^{15}$, OCH=CHR$^{15}$, O(CH$_2$CH$_2$O)$_p$R$^{15}$, O(CH$_2$)$_p$SO$_3$R$^{15}$, O(CH$_2$)$_p$NR$^{12}$R$^{13}$ and O(CH$_2$)$_p$N$^+$R$^{12}$R$^{13}$R$^{14}$ wherein n, p and $R^{12}$ to $R^{15}$ are as hereinbefore defined; with the proviso that in compounds of formula (III) at least two of $R^5$ to $R^8$ are not hydrogen; and salts solvates and physiologically functional derivatives thereof When one or more of $R^3$ to $R^8$ or $R^{11}$ to $R^{14}$ is a substituted $C_{1-6}$ alkyl group, or comprises a $C_{1-6}$ alkyl group the substituents may be the same or different and each is selected from hydroxy, halogen, $C_{1-6}$ alkyl, $C_{1-6}$ alkoxy, COR$^{16}$, nitrile, CO$_2$R$^{16}$, SO$_3$R$^{16}$, NR$^{17}$R$^{18}$, N$^+$R$^{17}$R$^{18}$R$^{19}$ wherein $R^{16}$ to $R^{19}$ are the same or different an each is selected from hydrogen or $C_{1-6}$ alkyl.

Suitably $R^1$ is methyl, ethyl or n-propyl and preferably $R^1$ is ethyl. Suitably $R^2$ is methyl, ethyl, n-propyl, n-butyl or n-pentyl. Preferably $R^2$ is n-butyl.

Preferably $R^5$ is hydrogen.

Suitably $R^7$ and $R^{7a}$ are selected from OR$^{15}$, S(O)$_n$R$^{15}$, OCOR$^{15}$, OCF$_3$, OCN, SCN, CHO, OCH$_2$OR$^{15}$, OCH=CHR$^{15}$, O(CH$_2$CH$_2$O)$_n$R$^{15}$, O(CH$_2$)$_p$SO$_3$R$^{15}$, O(CH$_2$)$_p$NR$^{12}$R$^{13}$ and O(CH$_2$)$_p$N$^+$R$^{12}$R$^{13}$R$^{14}$ wherein p is an integer from 1–4, n is an integer from 0–3 and, $R^{12}$, $R^{13}$, $R^{14}$ and $R^{15}$ are independently selected from hydrogen and optionally substituted $C_{1-6}$ alkyl. Preferably $R^7$ and $R^{7a}$ are OR$^{15}$.

Suitably $R^9$ and $R^{10}$ are hydrogen, methyl or ethyl. Preferably $R^9$ and $R^{10}$ are both hydrogen.

Suitably $R^4$ is pyridyl or phenyl optionally substituted, preferably at the 4- and/or 3-position by halogen, methyl, ethyl, methoxy, ethoxy, trifluoromethyl, hydroxy, carboxy or O(CH$_2$)$_3$SO$_3$H Perferably $R^4$ is unsubstituted phenyl.

In the compounds of the formula (II): suitably one or two, and preferably one, of $R^5$, $R^6$ and $R^8$ is other than hydrogen and suitably each is selected from $C_{1-4}$ alkyl, optionally substituted by fluoro, $C_{1-4}$ alkoxy, halogen and hydroxy. Most suitably, each is selected from methyl, methoxy, hydroxy, trifluoromethyl and halo. Preferably, $R^6$ is methoxy or bromo and $R^5$ and $R^8$ are hydrogen. Suitably, $R^{7a}$ is $C_{1-4}$ alkyl optionally substituted by fluoro, $C_{1-4}$ alkoxy, halogen or hydroxy. Most suitably, $R^{7a}$ is methoxy, hydroxy or trifluoromethyl and preferably $R^{7a}$ is methoxy.

In the compounds of the formula (III): suitably at least one and preferably two of $R^5$ to $R^8$ are hydrogen. Preferably at least one of $R^6$ and $R^7$ is not hydrogen. When $R^5$ to $R^8$ are other than hydrogen then they are suitably $C_{1-4}$ alkyl optionally substituted by fluorine, $C_{1-4}$ alkoxy, halogen or hydroxy, most suitably methyl, methoxy, hydroxy, trifluoromethyl or chloro and preferably methoxy.

In the compounds of the formula (IV): suitably two, three or four of $R^5$ to $R^8$ are hydrogen, the others being $C_{1-4}$ alkyl optionally substituted by fluoro, $C_{1-4}$ alkoxy, halogen or hydroxy and most suitably methyl, methoxy, hydroxy, trifluoromethyl or chloro and preferably methoxy.

In the compounds of formula (IVa): suitably at least one and preferably two of $R^5$ to $R^8$ are hydrogen. Preferably at least one of $R^6$ and $R^7$ is not hydrogen. When $R^5$ to $R^8$ are other than hydrogen then they are suitably $C_{1-4}$ alkyl optionally substituted by fluorine, $C_{1-4}$ alkoxy, halogen or hydroxy, most suitably methyl, methoxy, hydroxy, trifluoromethyl or chloro and preferably methoxy. Most preferably, $R^1$ is n-butyl, $R^2$ is ethyl, $R^3$, $R^5$, $R^8$, $R^9$ and $R^{10}$ are hydrogen, $R^4$ is pyridyl or optionally substituted phenyl and $R^6$ and $R^7$ are methoxy.

Preferred compounds of formula (I) are selected from the group consisting of:

(3R,5R)-3-Butyl-3-ethyl-2,3,4,5-tetrahydro-7,8-dimethoxy-5-phenyl-1,4-benzothiazepine-1,1-dioxide;

(3R,5R)-3-Butyl-3-ethyl-2,3,4,5-tetrahydro-7,8-dimethoxy-5-phenyl-1,4-benzothiazepine-4-ol 1,1-dioxide;

(+−)-Trans-3-butyl-3ethyl-2,3,4,5-tetrahydro-7,8-dimethoxy-5-phenyl-1,4-benzothiazepine-1,1-dioxide;
(+−)-Trans-3-butyl-3-ethyl-2,3,4,5-tetrahydro-7,8-dimethoxy-5-phenyl-1,4-benzothiazepine-4-ol 1,1-dioxide;
(3R,5R)-7-Bromo-3-butyl -3-ethyl-2,3,4,5-tetrahydro-8-methoxy-5-phenyl-1,4-benzothiazepine 1,1-dioxide;
(3R,5R)-7-Bromo-3-butyl-3-ethyl-2,3,4,5-tetrahydro-8-methoxy-5-phenyl-1,4-benzothiazepine4-ol 1,1-dioxide;
(3R,5R)-3-Butyl-3-ethyl-2,3,4,5-tetrahydro-5-phenyl-1,4-benzothiazepine-7,8-diol 1,1-dioxide;
(3R,5R)-3-Butyl-3-ethyl-2,3,4,5-tetrahydro-8-methoxy-5-phenyl-1,4-benzothiazepine-7-ol 1,1-dioxide;
(3R,5R)-3-Butyl-3-ethyl-2,3,4,5-tetrahydro-7-methoxy-5-phenyl-1,4-benzothiazepine-8-ol 1,1-dioxide;
(+−)-Trans-3-butyl-3-ethyl-2,3,4,5-tetrahydro-8-methoxy-5-phenyl-1,4-benzothiazepine 1,1-dioxide;
(+−)-Trans-3-butyl-3-ethyl-2,3,4,5-tetrahydro-5-phenyl-1,4-benzothiazepine-8-ol1,1-dioxide;
(+−)-Trans-3-butyl-3-ethyl-2,3,4,5-tetrahydro-5-phenyl-1,4-benzothiazepine-4,8-diol;
(+−)-Trans-3-butyl-3-ethyl-2,3,4,5-tetrahydro-8-methoxy-5-phenyl-1,4-benzothiazepine-7-carbaldehyde 1,1-dioxide;
(+−)-Trans-2-((3-butyl-3-ethyl-2,3,4,5-tetrahydro-8-methoxy-5-phenyl-1,4-benzothiazepine-7-yl)methoxy) ethanol S,S-dioxide;
(+−)-Trans-3-butyl-3-ethyl-2,3,4,5-tetrahydro-8-hydroxy-5-phenyl-1,4-benzothiazepine-7-carbaldehyde 1,1-dioxide;
(+−)-Trans-3-butyl-3-ethyl-2,3,4,5-tetrahydro-5-phenyl-1,4-benzothiazepine-8-thiol1,1-dioxide;
(+−)-Trans-3-butyl-3-ethyl-2,3,4,5-tetrahydro-5-phenyl-1,4-benzothiazepine-8-sulfonic acid-1,1-dioxide;
(7R,9R)-7-Butyl-7-ethyl-6,7,8,9-tetrahydro-9-phenyl-1,3-dioxolo(4,5-H)(1,4)-benzothiazepine 5,5-dioxide;
(+−)-Trans-3-butyl-3-ethyl-2,3,4,5-tetrahydro-8,9-dimethoxy-5-phenyl-1,4-benzothiazepine-1,1-dioxide;
(3R,5R)-3-butyl-3-ethyl-5-(4-fluorophenyl)-2,3,4,5-tetrahydro-7,8-dimethoxy-1,4-benzothiazpin-4-ol 1,1-dioxide;
(+−)-Trans-3-butyl-3-ethyl-2,3,4,5-tetrahydro-8-methoxy-5-phenyl-1,4-benzothiazepine-7-methanol S,S-dioxide;
(3R,5R)-3-butyl-3-ethyl-2,3,4,5-tetrahydro-8-methoxy-7-nitro-5-phenyl-1,4-benzothiazepine-1,1-dioxide;
(+−)-Trans-3-butyl-3-ethyl-2,3,4,5-tetrahydro-8-methoxy-7-(methoxymethyl)-5-phenyl-1,4-benzothiazepine 1,1-dioxide;
(3R,5R)-3-butyl-3-ethyl-2,3,4,5-tetrahydro-5-phenyl-1,4-benzothiazepine-7,8-diyl diacetate-1,1-dioxide;
(8R,10R)-8-Butyl-8-ethyl-2,3,7,8,9,10-hexahydro-10-1,4-dioxono(2,3-H)(1,4)-benzothiazepine 6,6-dioxide;
(3R,5R)-3-butyl-7,8-diethoxy-2,3,4,5-tetrahydro-5-phenyl-1,4-benzothiazepine 1,1-dioxide;
(+−)-Trans-3-butyl-8-ethoxy-3-ethyl-2,3,4,5-tetrahydro-5-phenyl-1,4-benzothiazepine-1,1-dioxide;
(+−)-Trans-3-butyl-3-ethyl-2,3,4,5-tetrahydro-8-isopropoxy-5-phenyl-1,4-benzothiazepine1,1-dioxide hydrochloride;
(+−)-Trans-3-butyl-3-ethyl-2,3,4,5-tetrahydro-5-phenyl-1,4-benzothiazepine-8-carbaldehyde-1,1-dioxide;
3,3-Diethyl-2,3,4,5-tetrahydro-7,8-dimethoxy-5-phenyl-1,4-benzothiazepine 1,1-dioxide;
3,3-Diethyl-5-(4-fluorophenyl)-2,3,4,5-tetrahydro-8-methoxy-1,4-benzothiazepine 1,1-dioxide;
3,3-Diethyl-2,3,4,5-tetrahydro-8-methoxy-5-phenyl-1,4-benzothiazepine1,1-dioxide;
3,3-Diethyl-2,3,4,5-tetrahydro-5-phenyl-1,4-benzothiazpin-4,8-diol1,1-dioxide;

(RS)-3,3-Diethyl-2,3,4,5-tetrahydro-4-hydroxy-7,8-dimethoxy-5-phenyl-1,4-benzothiazepine 1,1-dioxide;
(+−)-Trans-3-butyl-8-ethoxy-3-ethyl-2,3,4,5-tetrahydro-5-phenyl-1,4-benzothiazepine-4-ol-1,1-dioxide;
(+−)-Trans-3-butyl-3-ethyl-2,3,4,5-tetrahydro-8-isopropoxy-5-phenyl-1,4-benzothiazepine-4-ol 1,1-dioxide;
(+−)-Trans-3-butyl-3-ethyl-2,3,4,5-tetrahydro-7,8,9-trimethoxy-5-phenyl-1,4-benzothiazepine-4-ol 1,1-dioxide;
(3R,5R)-3-butyl-3-ethyl-2,3,4,5-tetrahydro-5-phenyl-1,4-benzothiazpin-4,7,8-triol 1,1-dioxide;
(+−)-Trans-3-butyl-3-ethyl-2,3,4,5-tetrahydro-4,7,8-trimethoxy-5-phenyl-1,4-benzothiazepine 1,1-dioxide;
(+−)-Trans-3-butyl-3-ethyl-5-phenyl-2,3,4,5-tetrahydro-7,8-dimethoxy-1,4-benzothiazepine-4-yl acetate S,S-dioxide;
3,3-Diethyl-2,3,4,5-tetrahydro-5-phenyl-1,4-benzothiazepine-8-ol 1,1-dioxide;
3,3-Diethyl-2,3,4,5-tetrahydro-7-methoxy-5-phenyl-1,4-benzothiazepine-8-ol 1,1-dioxide;
3,3-Dibutyl-2,3,4,5-tetrahydro-5-phenyl-1,4-benzothiazepine-8-ol 1,1-dioxide;
(+−)-Trans-3-Butyl-3-ethyl-2,3,4,5-tetrahydro-1,1-dioxo-5-phenyl-1,4-benzothiazepine-8-yl hydrogen sulfate;
(+−)-Trans-3-Butyl-3-ethyl-2,3,4,5-tetrahydro-1,1-dioxo-5-phenyl-1,4-benzothiazepine-8-yl dihydrogen phosphate;
3,3-Diethyl-2,3,4,5-tetrahydro-1,1-dioxo-5-phenyl-1,4-benzothiazepine-8-yl hydrogen sulfate;
3,3-Diethyl-2,3,4,5-tetrahydro-1,1-dioxo-5-phenyl-1,4-benzothiazepine-8-yl-dihydrogen phosphate;
(+−)-Trans-3-Butyl-3-ethyl-2,3,4,5-tetrahydro-1,1-dioxo-5-phenyl-1,4-benzothiazepine-8-yl aspartate; and
3,3-Diethyl-2,3,4,5-tetrahydro-1,1-dioxo-5-phenyl-1,4-benzothiazepine-8-yl aspartate.

Pharmaceutically acceptable salts are particularly suitable for medical applications because of their greater aqueous solubility relative to the parent, ie basic, compounds. Such salts must clearly have a pharmaceutically acceptable anion or cation. Suitable pharmaceutically acceptable acid addition salts of the compounds of the present invention include those derived from inorganic acids, such as hydrochloric, hydrobromic, phosphoric, metaphosphoric, nitric, sulphonic and sulphuric acids, and organic acids, such as acetic, benzenesulphonic, benzoic, citric, ethanesulphonic, fumaric, gluconic, glycollic, isothionic, lactic, lactobionic, maleic, malic, methanesulphonic, succinic, p-toluenesulphonic, tartaric and trifluoroacetic acids. The chloride salt is particularly preferred for medical purposes. Suitable pharmaceutically acceptable base salts include ammonium salts, alkali metal salts, such as sodium and potassium salts, and alkaline earth salts, such as magnesium and calcium salts.

Salts having a non-pharmaceutically acceptable anion are within the scope of the invention as useful intermediates for the preparation or purification of pharmaceutically acceptable salts and/or for use in non-therapeutic, for example, in vitro, applications.

The term "physiologically functional derivative" as used herein refers to any physiologically acceptable derivative of a compound of the present invention, for example, an ester, which upon administration to a mammal, such as a human, is capable of providing (directly or indirectly) such a compound or an active metabolite thereof.

A further aspect of the present invention is prodrugs of the compounds of the invention. Such prodrugs can be metabolised in vivo to give a compound according to the invention. These prodrugs may or may not be active in their own right.

The compounds of the present invention can also exist in different polymorphic forms, for example, amorphous and crystalline polymorphic forms. All polymorphic forms of the compounds of the present invention are within the scope of the invention and are a further aspect thereof.

The term "alkyl" as used herein refers, unless otherwise stated, to a monovalent straight or branched chain radical. Likewise, the term "alkoxy" refers to a monovalent straight or branched chain radical attached to the parent molecular moiety through an oxygen atom. The term "phenylalkoxy" refers to a monovalent phenyl group attached to a divalent $C_{1-6}$ alkylene group which is itself attached to the parent molecular moiety through an oxygen atom.

The compounds of formula (I) exist in forms wherein the carbon centres —$C(R^1)(R^2)$— and —$CHR^4$— is/are chiral. The present invention includes within its scope each possible optical isomer substantially free, i.e. as associated with less than 5%, of any other optical isomer(s), and mixtures of one or more optical isomers in any proportions, including racemic mixtures.

For the purposes of this specification, the absolute chiralities of the aforementioned carbon centres are given in the order —$C(R^1)(R^2)$—, then —$CHR^4$—.

In those cases where the absolute stereochemistry at —$C(R^1)(R^2)$— and —$CHR^4$— has not been determined, the compounds of the invention are defined in terms of the relative positions of the $R^1/R^2$ and $H/R^4$ substituents. Thus those compounds wherein the bulkier of the $R^1$ and $R^2$ substituents, i.e. the substituent of higher mass, and the $R^4$ substituent are both located on the same side of the thiazepine ring are referred to herein as "cis", and those compounds in which the bulkier of the $R^1$ and $R^2$ substituents are located on opposite sides of the ring are referred to as "trans" and are preferred. It will be evident to a skilled person that both "cis" and "trans" compounds of the invention can each exist in two enantiomeric forms which are individually designated "(+)-" or "(−)-" according to the direction of rotation of a plane of polarised light when passed through a sample of the compound. Cis or trans compounds of the invention in which the individual anantiomers have not been resolved are referred to herein using the prefix "(+−)-".

According to further aspects of the invention, there are also provided:

(a) compounds of formula (I) and pharmaceutically acceptable salts, solvates and physiologically functional derivatives thereof for use as therapeutic agents, particularly in the prophylaxis and treatment of clinical conditions for which a bile acid uptake inhibitor is indicated, for example, a hyperlipidemic condition, such as atherosclerosis;

(b) pharmaceutical compositions comprising a compound of formula (I) or one of its pharmaceutically acceptable salts, solvates, or physiologically functional derivatives, at least one pharmaceutically acceptable carrier and, optionally, one or more other physiologically active agents;

(c) the use of a compound of formula (I) or of a pharmaceutically acceptable salt, solvate, or physiologically functional derivative thereof in the manufacture of a medicament for the prophylaxis or treatment of a clinical condition for which a bile acid uptake inhibitor is indicated, for example, a hyperlipidemic condition, such as atherosclerosis;

(d) a method of inhibiting the absorption of bile acids from the intestine of a mammal, such as a human, which comprises administering an effective bile acid absorption inhibiting amount of a compound of formula (I) or of a pharmaceutically acceptable salt, solvate, or physiologically functional derivative thereof to the mammal;

(e) a method of reducing the blood plasma or serum concentrations of LDL and VLDL cholesterol in a mammal, such as a human, which comprises administering an effective cholesterol reducing amount of a compound of formula (I) or of a pharmaceutically acceptable salt, solvate, or physiologically functional derivative thereof to the mammal;

(f) a method of reducing the concentrations of cholesterol and cholesterol ester in the blood plasma or serum of a mammal, such as a human, which comprises administering an effective cholesterol and cholesterol ester reducing amount of a compound of formula (I) or of a pharmaceutically acceptable salt, solvate, or physiologically functional derivative thereof to the mammal;

(g) a method of increasing the fecal excretion of bile acids in a mammal, such as a human, which comprises administering an effective bile acid fecal excretion increasing amount of a compound of formula (I) or of a pharmaceutically acceptable salt, solvate, or physiologically functional derivative thereof to the mammal;

(h) a method for the prophylaxis or treatment of a clinical condition in a mammal, such as a human, for which a bile acid uptake inhibitor is indicated, for example, a hyperlipidemic condition, such as atherosclerosis, which comprises administering a therapeutically effective amount of a compound of the formula (I) or of a pharmaceutically acceptable salt, solvate, or physiologically functional derivative thereof to the mammal;

(i) a method of reducing the incidence of coronary heart disease-related events in a mammal, such as a human, which comprises administering an effective coronary heart disease-related events reducing amount of a compound of formula (I) or of a pharmaceutically acceptable salt, solvate, or physiologically functional derivative thereof;

(j) a method of reducing the concentration of cholesterol in the blood plasma or serum of a mammal, such as a human, which comprises administering an effective cholesterol reducing amount of a compound of formula (I);

(k) processes for the preparation of compounds of formula (I) (including salts, solvates and physiologically functional derivatives thereof as defined herein); and (l) novel chemical intermediates in the preparation of compounds of formula (I).

(m) the compounds of Synthetic Examples 1–53 as hereinafter disclosed.

Hereinafter all references to "compound(s) of formula (I)" refer to compound(s) of formula (I) as described above together with their salts, solvates and physiologically functional derivatives as defined herein.

The amount of a compound of formula (I) which is required to achieve the desired biological effect will, of course, depend on a number of factors, for example, the specific compound chosen, the use for which it is intended, the mode of administration and the clinical condition of the recipient. In general, a daily dose is in the range of from 0.3 mg to 100 mg (typically from 3 mg to 50 mg) per day per kilogram bodyweight, for example, 3–10 mg/kg/day. An intravenous dose can, for example, be in the range of from 0.3 mg to 1.0 mg/kg, which can conveniently be administered as an infusion of from 10 ng to 100 ng per kilogram per minute. Infusion fluids suitable for this purpose can contain, for example, from 0.1 ng to 10 mg, typically from 1 ng to 10 mg, per millilitre. Unit doses can contain, for example, from 1 mg to 10 g of the active compound. Thus ampoules for injection can contain, for example, from 1 mg to 100 mg and orally administrable unit dose formulations, such as tablets or capsules, may contain, for example, from 1.0 to 1000 mg, typically from 10 to 600 mg. In the case of pharmaceutically acceptable salts, the weights indicated above refer to the weight of the benzothiazepine ion derived from the salt.

For the prophylaxis or treatment of the conditions referred to above, the compounds of formula (I) can be used as the compound per se, but are preferably presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present including other compounds of formula (I). The pharmaceutical compositions of the invention can be prepared by any of the well known techniques of pharmacy consisting essentially of admixing the components.

Pharmaceutical compositions according to the present invention include those suitable for oral, rectal, topical, buccal (e.g. sub-lingual) and parenteral (e.g. subcutaneous, intramuscular, intradermal, or intravenous) administration, although the most suitable route in any given case will depend on the nature and severity of the condition being treated and on the nature of the particular compound of formula (I) which is being used. Enteric-coated and enteric-coated controlled release formulations are also within the scope of the invention. Suitable enteric coatings include cellulose acetate phthalate, polyvinylacetate phthalate, hydroxypropylmethylcellulose phthalate and anionic polymers of methacrylic acid and methacrylic acid methyl ester.

Pharmaceutical compositions suitable for oral administration can be presented in discrete units, such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. As indicated, such compositions can be prepared by any suitable method of pharmacy which includes the, step bringing into association the active compound and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or moulding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Moulded tablets can be made by moulding, in a suitable machine, the powdered compound moistened with an inert liquid diluent.

Pharmaceutical compositions suitable for buccal (sub-lingual) administration include lozenges comprising a compound of formula (I) in a flavored base, usually sucrose and acacia or tragacanth, and pastilies comprising the compound in an inert base such as gelatin and glycerin or sucrose and acacia.

Pharmaceutical compositions suitable for parenteral administration conveniently comprise sterile aqueous preparations of a compound of formula (I), preferably isotonic with the blood of the intended recipient. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of the active compound.

Pharmaceutical compositions suitable for rectal administration are preferably presented as unit-dose suppositories. These can be prepared by admixing a compound of formula (I) with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof The active compound is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain the active compound in an optionally buffered, aqueous solution, dissolved and/or dispersed in an adhesive, or dispersed in a polymer. A suitable concentration of the active compound is about 1% to 35%, preferably about 3% to 15%. As one particular possibility, the active compound can be delivered from the patch by electrotransport or iontophoresis, for example, as described in *Pharmaceutical Research*, 3(6), 318 (1986).

The compounds of the invention can be prepared by conventional methods known to a skilled person or in an analogous manner to processes described in the art.

For example, compounds of the formula (I) wherein $R^3$ is hydrogen can be prepared by oxidation of the corresponding compound of the formula (V):

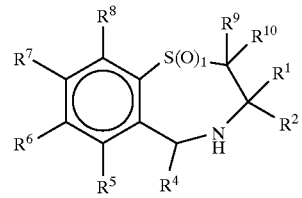

(V)

wherein $R^1$ to $R^{10}$ are as hereinbefore defined and l is 0 or 1. This oxidation may suitably be carried out by reaction with a peroxide, for example hydrogen peroxide in the presence of trifluoroacetic acid at a non-extreme temperature, e.g. −20° C. to 50° C. and preferably at −10° C. to 10° C. The compound of the formula (V) where l is 1 may be prepared from the corresponding compound where l is 0 by partial oxidation using a peroxide as described above.

Compounds of formula (V) can be prepared by reducing the imine bond of a compound of formula (VI)

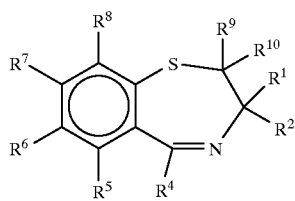

(VI)

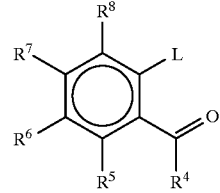

(IX)

wherein $R^1$ to $R^{10}$ are as hereinbefore defined, using, for example, a boron compound, such as borane, in a suitable solvent, for example an ether such as THF, or catalytic hydrogenation using, for example, a palladium catalyst, such as 10% Pd/C at a non-extreme temperature, for example −20° C. to 100° C. and preferably −10° C. to 50° C.

Compounds of formula (VI) as herein defined as well as each possible optical isomer substantially free, i.e., associated with less than 5% of any other optical isomer(s), and mixtures of one or more optical isomers in any proportions, including racemic mixtures are considered to be novel and constitute a further aspect of the present invention.

Compounds of formula (VI) can be prepared by cyclising compounds of formula (VII)

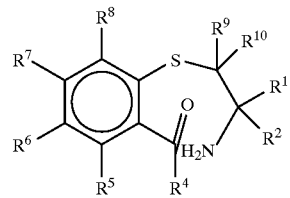

(VII)

wherein $R^1$ to $R^8$ are as hereinbefore defined, by, for example, azeotropic distillation or refluxing in the presence of a suitable drying agent, such as molecular sieves, in a suitable solvent, for example, 2,6-lutidine, in the presence of an acid, such as HCl.

Compounds of formula (VII) can be prepared by reacting a compound of formula (VIII)

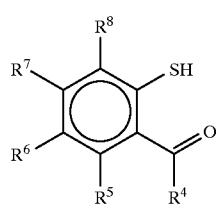

(VIII)

wherein $R^4$ to $R^8$ are as hereinbefore defined, with the appropriately substituted aziridine, typically in a polar solvent, for example, methanol.

Compounds of formula (VII) can also be prepared by reacting a compound of formula (IX)

wherein $R^4$ to $R^8$ are as hereinbefore defined and L is a suitable leaving group, for example, halogen, with a compound of formula $HSC(R^9)(R^{10})C(R^1)(R^2)Nh_2$ wherein $R^1, R^2$ $R^9$ and $R^{10}$ are as hereinbefore defined.

Compounds of formula (IX) can be prepared by reacting the corresponding acid with a compound of formula $R^4H$ wherein $R^4$ is as hereinbefore defined, typically by a Friedel-Crafts reaction using, for example, aluminium chloride.

Compounds of formula (VIII) can be prepared by reacting a compound of formula (X)

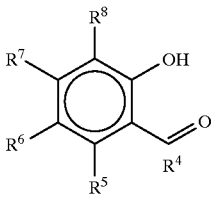

(X)

wherein $R^5$ to $R^8$ are as hereinbefore defined with a non-nucleophilic base such as sodium hydride followed by treatment of the resulting salt with N,N-dimethylthiocarbamoyl chloride, pyrolysis of the resulting O-aryldialkylthiocarbamate to the S-aryldialkylthiocarbamate (for example in a high boiling solvent such as tetradecane at a temperature of about 255° C.), and hydrolysis (for example with a strong base such as KOH).

Alternatively, compounds of formula (VIII) can be prepared by reacting compounds of formula (IX) with sodium hydrosulfide (NaSH).

The starting materials as hereinbefore defined can be obtained commercially or prepared by methods known to those skilled in the art or obtainable from the chemical literature, for example, the aziridines can be prepared from the corresponding 2-substituted 2-aminoethanols.

Compounds of the formula (V) wherein one or more of $R^5$ to $R^8$ is halo may be converted to compounds of the formula (V) wherein $R^5$ to $R^8$ is a different functional group by methods known to those skilled in the art or readily available from the literature.

Compounds of formula (I) wherein $R^3$=OH can be prepared from the corresponding compounds of formula (I) wherein $R^3$=H by oxidation with, for example, m-chloroperbenzoic acid.

The compounds of formula (I) substantially free, of other optical isomers can be obtained either by chiral synthesis, for example, by the use of the appropriate chiral starting material(s), such as the aziridine, or by resolution of the products obtained from aciral syntheses, for example, by chiral hplc or by classical resolution with chiral acids.

Optional conversion of a compound of formula (I), or a compound of formula (I) comprising a basic substituent, to a corresponding acid addition salt may be effected by reaction with a solution of the appropriate acid, for example, one of those recited earlier. Optional conversion of a compound of formula (I) comprising an acidic substituent to a corresponding base salt may be effected by reaction with a solution of the appropriate base, for example, s odium hydroxide. Option al conversion to a physiologically functional derivative, such as an ester, can be carried out by methods known to those skilled in the art or obtainable from the chemical literature.

In addition, compounds of the formula (I) may be converted to different compounds of the formula (I) by standard methods known or available from the literature to those skilled in the art, for example by alkylation of a hydroxy group.

For a better understanding of the invention, the following Examples are given by way of illustration and are not to be construed in any way as limiting the scope of the invention.

SYNTHETIC EXAMPLE 1

Preparation of (3R,5R)-3-butyl-3-ethyl-2,3,4,5-tetrahydro-7,8-dimethoxy-5-phenyl-1-4-benzothiazepine 1,1-dioxide (a) Ethyl 2-aminobutyate hydrochloride A slurry of 2-aminobutyric acid (100 g, Aldrich) in absolute ethanol (300 ml) wa s stirred under nitrogen at 0° C. and thionyl chloride (120.8 g) was added dropwise. The reaction was stirred overnight at 0° C. and then gradually warmed to room temperature. The resulting white slurry was heated under reflux for 3 hours, left to cool for 10 minutes, then poured into chilled diethyl ether (600 ml), with hand stirring. The suspension was filtered and the solid product dried to give the desired product (150 g) as a white solid. $^1$H NMR consistent with proposed structure.

(b) Ethyl 2-benzylideneamnobutyrate

A solution of the product from step (a) (149.6 g), magnesium sulfate (74.3 g), and triethylamine (246 ml) in dichtoromethane (1500 ml) was stirred at room temperature under nitrogen and benzaldehyde (94.9 g, Aldrich) was added dropwise. The mixture was stirred at room temperature for 3 hours then filtered. The filtrate was concentrated, triturated in diethyl ether, filtered and concentrated to yield the desired product as a yellow oil (174 g), $^1$H NMR consistent with the proposed structure.

(c) (+−)-Ethyl 2-benzylideneamino-2-ethylhexanoate

Sodium hydride (32.5 g, 60% dispersion in oil) and N,N-dimethylfomiamide (DMF) (700 ml) were stirred under nitrogen at room temperature and a solution of the product from step (b) (178.1 g) in DMF was added dropwise. After 2 hours stirring at room temperature, a solution of butyl iodide (149.5 g) in DMF was added dropwise and the reaction left stirring for a further 2 hours. The reaction was poured into an ice cold mixture of water (560 ml), diethyl ether (300 ml) and ammonium chloride (120 g). The resulting organic layer was dried over potassium carbonate then concentrated to give the desired product as a brown oil (220 g).

(d) (+−)-Ethyl 2-amino-2-ethylhexanoate

The product from step (c) (233.0 g) was partitioned between petroleum ether and 10% w/w hydrochloric acid (421 ml) and stirred at room temperature for 2 hours. The aqueous layer was extracted twice with petroleum ether and then chilled with ethyl acetate in an ice-salt bath. Sodium hydroxide pellets were added to the mixture until the aqueous layer was at pH 10. The latter was extracted twice with ethyl acetate and the combined ethyl acetate layers were dried over potassium carbonate, then concentrated and vacuum distilled to give the desired product as a colourless oil. $^1$H NMR consistent with the proposed structure.

(e) (R)-2-Amino-2-ethylhexanoic acid

A suspension of pig liver esterase (0.1 g, Sigma-Aldrich-Fluka) in water was added to an aqueous solution of the product from step (d) (100 g). When addition was complete, the pH of the mixture was adjusted to 9.7 using 1N aqueous NaOH and maintained at this value by the addition of further 1N NaOH. After the addition of a predetermined amount of 1N aqueous NaOH (85 g over 10 hours), the mixture was washed with diethyl ether to remove unreacted (S)-ethyl 2-amino-2-ethyl-hexanoate. The remaining aqueous phase was evaporated in vacuo to give a white solid comprising the titled compound and its sodium salt.

(f) (R)-2-Amino-2-ethylhexan-1-ol

The product (20 g) from step (e) was added to a 1M solution of lithium aluminum hydride (1.5 molar equivalents) in THF and the mixture was refluxed for 3 hours, then stirred for 16 hours at room temperature. The mixture was cooled to about 0° C., then quenched with water and 1N aqueous NaOH. The resulting solid was broken up with additional water and the suspension was heated at 50° C. for 5 minutes, then cooled to room temperature. Diethyl ether (100 ml) was added, the mixture was stirred and filtered. The diethyl ether layer was separated, dried and concentrated in vacuo to give the desired product as an oil (82% yield), $^1$H NMR consistent with the proposed structure.

(g) (R)-2-Amino-2-ethylhexyl hydrogen sulfate

The product (20.0 g) from step (f) was dissolved in dichioromethane (170 ml) and treated with chlorosulfonic acid (26.8 g). The reaction mixture was stirred at room temperature for 17 hours. A major part of the solvent was removed by distillation and the resulting slurry was diluted with acetone, filtered and dried to get a white solid. $^1$H NMR consistent with the proposed structure.

(h) 2-Hydroxy-4,5-dimethoxybenzaldehyde

A 1.0M solution of boron trichloride (210 ml, Aldrich) in dichloromethane was added to benzoyl chloride (130 g. Aldrich) in benzene (350 ml). Next, 3,4-dimethoxyphenol (30.0 g, Aldrich) in benzene (130 ml) was added and the reaction mixture was stirred at room temperature for 2½ hours. 50% NaOH (55 ml) was then added and the mixture was stirred for 15 minutes. The organic layers were separated, dried and concentrated in vacuo. The resulting residue was triturated with $^1$N NaOH for 40 minutes then filtered. The aqueous basic filtrate was acidified with conc. HCl to give the title product as a yellow solid (25.9 g), mp 104–105° C. $^1$H NMR was consistent with the proposed structure.

(i) O-(2-Benzoyl4,5-dimethoxyphenyl N,N-diethylthiocarbamate

Triethylamine (106.3 g, Aldrich)), 4-dimethylaminopyridine (6.5 g, Aldrich) and diethylthiocarbamoyl (86.4 g) was added to the product (130.4 g) from step(h) to 1 L of dioxane. The reaction mixture was stirred at reflux for 22 hours, cooled to room temperature, then filtered. The filtrate was concentrated in vacuo and 1N HCl (600 ml) was added followed by diethyl ether (500 ml). The mixture was allowed to stand for 45 minutes, then filtered. The solids were washed thoroughly with diethyl ether and dried in a vacuum oven to afford the title product as a yellow solid (120.5 g), mp 94–95° C. $^1$H NMR was consistent with the proposed structure.

(j) S-(2-Benzoyl-4,5-dimethoxyphenyl) N,N-diethylthiocarbamate

A slurry of the product (60.4 g) from step (i) in tetradecane (250 ml) was heated to an internal temperature of 250° C. and kept there for a period of 25 minutes. The reaction mixture was cooled with an ice bath. The solvent was decanted and the residue was triturated with diethyl ether (100 ml) to give the title product (43.4 g) as a beige solid, mp 114–116° C. $^1$H NMR was consistent with the proposed structure.

(k) 2-Mercapto4,5-dimethoxybenzophenone

Potassium hydroxide pellets (58.6 g) was slowly added to a solution of the product (85.0 g) from step (j) dissolved in 1 L of methanol/THF (1:1). After refluxing for 3 hours, the reaction mixture was cooled to room temperature and concentrated in vacuo. The resulting residue was triturated with 1N HCl then extracted with EtOAc. The organic layer was separated, washed with 2×250 ml of 1N HCl then washed with 3×400 ml of 1N NaOH. The aqueous basic layers were combined and acidified with conc. HCl to afford the title product (54.8 g) as a gold solid. $^1$H NMR was consistent with the proposed structure.

(1),(R)-2-(2-Amino-2-ethylhexylthio)4,5-dimethoxybenzophenone

The product (48.8 g) from step (g) was dissolved in water (250 ml) and to this solution the product (54.2 g) from step (k) in butyl acetate (300 ml) was added. The reaction mixture was stirred and heated to an internal temperature of 93° C. and NaOH (18.9 g) in water (250 ml) was added dropwise. After complete addition, the reaction was stirred an additional 25 minutes at 93° C., then cooled to room temperature. The organic layer was separated, dried and concentrated to give the title product (78.5 g) as an orange-brown oil. Treatment of the free base with ethereal HCl afforded the hydrochloride salt as a light yellow solid, mp 75–78° C. $^1$H NMR consistent with the proposed structure.

(m) (3R)-3-Butyl-3-ethyl-2,3-dihydro-7,8-dimethoxy-5-phenyl-1,4-benzothiazepine

The product (78.0 g) from step (1) was dissolved in 2,6-lutidine (400 ml), added p-toluenesulfonic acid (0.70 g) and the reaction mixture was refluxed using a Dean Stark trap. The reaction was refluxed for a period of 22 hours during which time solvent was removed from the apparatus and then replaced with fresh solvent. The reaction mixture was concentrated in vacuo and the residue was treated with 5% NaHCO$_3$(300 ml) and EtOAc(300 ml). The EtOAc layer was separated, washed with brine, dried and concentrated in vacuo to give a dark red oil. Chromatography on silica gel, using hexane: EtOAc(4:1) as eluant, afforded the desired product (64.1 g) as a light brown oil. $^1$H NMR consistent for the proposed structure.

(n) (3R,5R)-3-Butyl-3-ethyl-2,3,4,5-tetrahydro-7,8-dimethoxy-5-phenyl-1,4-benzothiazepine A 1M solution of diborane in THF (200 ml) was added to a solution of the product (64.0 g) from step (m) in THF (350 ml). The reaction mixture was stirred at room temperature for a period of 17 hours, then 6N HCl (150 ml) was added and the solution was concentrated in vacuo to remove THF. The aqueous residue was basified with 50% NaOH and extracted with EtOAc. The EtOAc layer was separated, dried and concentrated in vacuo to afford an oil which was chromatographed on silica gel, using hexane: EtOAc (85:15) as eluant, to give the title product (25.5 g) as a beige solid, mp 64–66° C. $^1$H NMR consistent for proposed structure.

(o) (3R,5R)-3-Butyl-1-3-ethyl-2,3,4,5-tetrahydro-7,8-dimethoxy-5-phenyl-1,4-benzothiazepine 1,1-dioxide A solution of the product (25.5 g) from step (n) in trifluoroacetic acid (125 ml) was added to 30% H$_2$O$_2$ (18.8 g) in trifluoroacetic acid (100 ml). The reaction mixture was stirred at room temperature for 17 hours, then poured into water (800 ml) followed by the addition of 50% NaOH until the mixture reached a pH of 10. The reaction mixtre was layered with EtOAc and stirred for 1 hour. The organic layer was separated, dried and concentrated in vacuo to afford solids which were recrystallized from EtOH to afford the title product (18.5 g) as a white solid, mp 148–149° C.

Analysis: Calcd: C 66.16; H 7.48; N 3.35; S 7.68; Found: C 66.01; H 7.56; N 3.31; S 7.74;

$^1$H NMR (DMSO-d$_6$), δ; 0.74–0.86(6H, m); 1.07–1.39 (4H, m); 1.39–2.20 (4H, m); 3.33 (2H, q); 3.44 (3H, s); 3.83 (3H, s); 5.92 (1H, d); 6.11 (1H, s); 7.33–7.48 (6H, m).

SYNTHETIC EXAMPLE 2

Preparation of (3R,5R)-3-Butyl-3-ethyl-2,3,4,5-tetrahydro-7,8-dimethoxy-5-phenyl-1,4-benzothiazepine-4-ol 1,1-dioxide Oxone (146.7 g Aldrich) in water (550 ml) was added to a solution of the product (18.4 g) from Synthetic Example 1(n) in MeOH (500 ml). The reaction mixture was stirred at room temperature for 17 hours, then cautiously basified with 50% NaOH. This heterogeneous mixture was layered with EtOAc and stirred for 1 hour. The organic layer was separated, dried and concentrated in vacuo to get a pink solid. Chromatography on silica gel, using hexane: EtOAc (65.35) as eluant, afforded the title product (6.7 g) as a white solid, mp 174–175° C.

Analysis: Calcd: C 63.72; H 7.21; N 3.23; S 7.39; Found: C 63.81; H 7.22; N 3.19; S 7.47;

$^1$H NMR(DMSO-d$_6$), δ: 0.77–0.90 (6H, m); 1.10–2.17 (8H,m); 3.27–3.45 (5H, m); 3.84 (3H, s); 6.14 (1H, s); 6.38 (1H, s); 7.30–7.53 (5H, m); 7.97 (1H, s).

SYNTHETIC EXAMPLE 3

Preparation of (+−)-Trans-3-butyl-3-ethyl-2,3,4,5-tetrahydro-7,8-dimethoxy-5-phenyl-1,4-benzothiazepine 1,1-dioxide (a) (+−)-2-Amino-2-ethylhexan-1-ol Lithium aluminum hydride (22.2 g) was added to anhydrous diethyl ether (450 ml) under nitrogen. The product (129.0 g) from Synthetic Example 1(d) was diluted with diethyl ether (40 ml) and added dropwise. The reaction was refluxed for 1 hour then cooled to room temperature. 1M sodium hydroxide (23 ml) was added dropwise followed by deionised water. The resulting suspension was filtered and the filtrate concentrated to give the desired product as a colorless oil (87.9 g). $^1$H NMR consistent with the proposed structure.

(b) (+−)-2-Butyl-2-ethylaziridine

Acetonitrile (150 ml) and the product (20.0 g) from step (a) were mixed under nitrogen, cooled to 2–3° C. and chlorosulphonic acid (16.0 g) Aldrich) was added dropwise keeping the temperature below 10° C. The coolant was removed and the slurry left to stir for 80 minutes at room temperature. The reaction was concentrated in vacuo and co-distilled with water (50 ml). 50% Aqueous sodium hydroxide (55.2 g) and water (50 ml) were added and the mixture was distilled at atmospheric pressure. The organic layer was collected from the distillate and dried with solid potassium hydroxide to give the desired product (12.8 g). $^1$H NMR consistent with proposed structure.

(c) (+−)-3-Butyl-3-ethyl-2,3-dihydro-7,8-dimethoxy-5-phenyl-1,4-benzothiazepine

The product (14.7 g) from Synthetic Example 1(k), in 2,6-lutidine (50 ml), was added to a solution of the product (6.5 g) from step (b) in 2,6-lutidine (200 ml). The reaction mixture was stirred for 1 hour, conc. HCl (4.4 ml) was added and then refluxed with a Dean-Stark trap for 17 hours. The reaction mixture was concentrated in vacuo and the residue was partitioned between 5% NaHCO, and EtOAc. The organic layer was separated, dried and concentrated to get an oil which was chromatographed on silica gel, using hexane: EtOAc (7:3) as eluant to afford the desired product (12.0 g) as an oil. $^1$H NMR consistent with proposed structure.

d) (+−)-Trans-3-butyl-3-ethyl-2,3,4,5-tetrahydro-7,8-dimethoxy-5-phenyl-1,4-benzothiazepine 1,1-dioxide The title compound was prepared following the procedures of Synthetic Example 1 (n)–(o) using the product from step (c) to give a white solid, mp 146–147° C.

Analysis (0.50 H$_2$O); Calcd: C 64.54; H 7.35; N 3.24; S 7.40; Found: C 64.76; H 7.56; N 3.28; S 7.52; $^1$H NMR (DMSO-d$_6$), δ: 0.74–0.86 (6H, m); 1.07–1.39 (4H, m); 1.40–2.20 (4H, m); 3.33 (2H, q); 3.44 (3H, s); 3.83 (3H, s); 5.92 (1H d); 6.11 (1H, s); 7.30–7.48 (6H, m)

SYNTHETIC EXAMPLE 4

Preparation of (+−)-Trans-3-butyl-3-ethyl-2,3,4,5-tetrahydro-7,8-dimethoxy-5-phenyl-1,4-benzothiazepine-4-ol 1,1-dioxide Oxone (7.3 g, Aldrich) in water (100 ml) was added to a solution of the product (1.7 g) from Synthetic Example 3(d) in MeOH (100 ml). The reaction mixture was stirred at room temperature for a period of 17 hours and water and EtOAc were added. After stirring for 1 hour, the organic layer was separated, dried and concentrated to give a foam. Chromatography on silica gel, using hexane: EtOAc (4:1) as eluant, gave the desired product (1.2 g) as a white solid, mp 172–174° C.

Analysis: Calcd: C 63.72; H 7.21; N 3.23; S 7.39; Found: C 63.79; H 7.26; N 3.18; S 7.47; $^1$H NMR (DMSO-d$_6$), δ: 0.78–0.90 (6H, m); 1.14–2.14(8H, m); 3.27–3.41 (5H, m); 3.84 (3H, s); 6.13 (1H, s); 6.37 (1H, s); 7.34–7.53 (5H, m); 7.96 (1H, s).

SYNTHETIC EXAMPLE 5

Preparation of (3R,5R)-7-Bromo-3-butyl-3-ethyl-2,3,4,5-tetrahydro-8-methoxy-5-phenyl-1,4-benzothiazepine 1,1-dioxide (a) O-(2-benzoyl-5-methoxyphenyl)dimethylthiocarbamate Sodium hydride (8.8 g, Aldrich) was added slowly to a solution of 2-hydroxy-4-methoxybenzophenone (50.0 g, Aldrich) in 300 ml of dimethylformamide. Hexamethylphosphoramiide (43.0 g) was then added dropwise and stirred at room temperature for 2 hours. Dimethyithiocarbamoyl chloride (37.0 g, Aldrich) was added and stirred overnight at 50° C. The reaction mixture was poured into deionized water (300 mL) and extracted with a petroleum ether/chloroform (1:4) mixture. The organic layer was washed with 10% sodium hydroxide, brine and concentrated to give the title product as a yellow solid (40.0 g). $^1$H NMR was consistent with proposed structure.

(b) S-(2-Benzoyl-5-methoxyphenyl)dimehylthiocarbamate

The product (97.4 g) from step (a) was suspended in tetradecane (500 mL) and heated to an internal temperature of 255° C. for 30 minutes. After cooling to room temperature, the reaction mixture was chromatographed on silica gel using hexane, then hexanes/ethyl acetate (7:3) as eluants to afford the title product (65.0 g) as a tan solid, mp 95–97° C. $^1$H NMR was consistent with proposed structure.

(c) 2-Mercapto-4-methoxybenzophenone

Potassium hydroxide pellets (20.0 g) were slowly added to a solution of the product (28.0 g) from step (b) dissolved in 800 ml methanol/tetrahydrofuran (1:1). After refluxing for 4 hours, the reaction was cooled to room temperature, methylene chloride was added and the solution was extracted with 5% hydrochloric acid. The organic layer was dried and concentrated. Chromatography on silica gel using hexanes/ethyl acetate (99:1) as the eluant afforded the title product (17.1 g) as an orange oil. $^1$H NMR consistent with proposed structure.

(d) (R)-2-(2-Amino-2-ethylhexylthio)-4-methoxyhenzophenone

This compound was prepared following the procedure of Synthetic Example 1(1), using the product (46.4 g) from step (c) and the product (44.6 g) from Synthetic Example 1 (g). Concentration of the organic layer afforded the title product (66.5 g) as a red oil. $^1$H NMR consistent with proposed structure.

(e) (3R)-3-Butyl-3-ethyl-2,3-dihydro-8-methoxy-5-phenyl-1,4-benzothiazepine

This compound was prepared following the procedure of Synthetic Example 1(m), using the product (66.5 g) from step (d). Chromatography on silica gel, using hexane:EtOAc (9:1) as eluant, afforded the title compound (54.5 g) as a yellow oil. $^1$H NMR consistent with the proposed structure.

(f) (3R,5R)-3-Butyl-3-ethyl-2,3,4,5-tetrahydro-8-methoxy-5-phenyl-1,4-benzothiazepine This compound was prepared following the procedure of Synthetic Example 1(n), using the product (54.4 g) from step (e). Chromatography on silica gel, using hexane:EtOAc (9:1) as eluant, gave the title product (22.8 g) as an orange oil. $^1$H NMR consistent with the proposed structure.

(g) (3R,5R)-7-Bromo-3-butyl-3-ethyl-2,3,4,5-tetrahydro-8-methoxy-5-phenyl-1,4-benzothiazepine Bromine (18.6 g) was added to a solution of the product (10.4 g) from step (f) dissolved in glacial acetic acid (150 ml). The reaction mixture was stirred at room temperature for 2 hours. Acetic acid was removed in vacuo, added another 100 ml and concentrated in vacuo. The resulting residue was dissolved in EtOAc and washed with sodium metabisulfite and 1N NaOH. The organic layer was separated, dried and concentrated in vacuo to give a brown oil which was then converted to the hydrochloride salt with ethereal HCl. This solid was filtered, washed with ether and then treated with 1N NaOH and EtOAc to get the title product (8.9 g) as an orange oil. $^1$H NMR consistent with the proposed structure.

(h) (3R,5R)-7-Bromo-3-butyl-3-ethyl-2,3,4,5-tetrahydro-8-methoxy-5-phenyl-1,4-benzothiazepine 1,1-dioxide This compound was prepared following the procedure of Synthetic Example 1(o), using the product (8.2 g) from step (g). Chromatography on silica gel, using hexane: EtOAc (4:1) as eluant, afforded a foam which upon trituration in ether gave the title product (5.0 g) as a white solid, mp 132–134° C.

Analysis: Calcd; C 56.65; H 6.05; N 3.00; Br 17.13; S 6.87; Found: C56.71; H 6.01; N 2.94; Br 17.07; S 6.95; $^1$HNMR (DMSO-d$_6$), δ: 0.64–0.81 (6H, m); 0.97–1.19 (4H, m); 1.22–1.50 (2H, m) 1.69–1.78 (1H, m); 1.98–2.06 (1H, m); 2.67 (1H, d,); 3.39 (2H, q,); 3.92 (3H, s); 5.88 (1H, d); 6.63 (1H, s); 7.29–7.43 (5H, m); 7.55 (1H, s)

SYNTHETIC EXAMPLE 6

Preparation of (3R,5R)-7-Bromo-3-butyl-3-ethyl-2,3,4,5-tetrahydro-8-methoxy-5-phenyl-1,4-benzothiazepine-4-ol 1,1-dioxide Meta-chloroperbenzoic acid (57–86%, 0.90 g, Aldrich) in CH$_2$Cl$_2$ (50 ml) was added to a solution of the product (2.4 g) from Synthetic Example 5(h) in CH$_2$Cl$_2$ (50 ml). The reaction was stirred at room temperature for 1 hour, then 5% NaHCO$_3$ (100 ml) was added and the mixture stirred for 30 minutes. The organic layer was separated, dried and concentrated in vacuo to give a foam. Chromatography on silica gel, using hexane: EtOAc (9:1) as eluant gave a foam which upon trituration with ether afforded the title product (1.3 g) as a white solid, mp 202–204° C.

Analysis: Calcd: C 54.77; H 5.85; N 2.90; Br 16.56; S 6.65; Found: C 54.92; H 5.90; N 2.85; Br 16.65; S 6.75; $^1$H NMR (DMSO-d$_6$), δ: 0.75–0.86 (6H, m); 1.05–1.41 (5H, m); 1.43–1.64 (1H, m); 1.66–1.79 (1H, m); 1.83–2.49 (1H, m); 3.46 (2H, s); 3.93 (3H, s); 6.33 (1H, s); 6.67 (1H, s); 7.30–7.50 (6H, m); 8.07 (1H, s)

SYNTHETIC EXAMPLE 7

Preparation of (3R,5R)-3-Butyl-3-ethyl-2,3,4,5-tetrahydro-5-phenyl-1,4-benzothiazepine-7,8-diol 1,1-dioxide The product (5.0 g) from Synthetic Example 1(o) was dissolved in glacial acetic acid (36 ml) and 48% HBr (36 ml) and allowed to stir at reflux for 2 hours. The reaction mixture was poured into an ice water mixture then basified with 50% NaOH to a pH of 7. The reaction mixture was filtered to get a solid which was chromatographed on silica gel, using hexane: EtOAc (3:2) as eluant, to give the title product (1.6 g) as a white solid, mp 117–118° C.

Analysis (0.30 H$_2$O): Calcd: C 63.87; H 7.04; N 3.55; S 8.12; Found: C 63.86; H 7.09; N 3.51; S 8.18; $^1$H NMR (DMSO-d$_6$), δ: 0.76 (3H, t); 0.81 (3H, t); 1.08–2.41 (8H, m); 3.24 (2H, q); 5.83 (1H, d); 6.03 (1H, s); 7.31–7.42 (6H, m); 9.60 (3H, bs)

SYNTHETIC EXAMPLE 8

Preparation of (3R,5R)-3-Butyl-3-ethyl-2,3,4,5-tetrahydro-8-methoxy-5-phenyl-1,4-benzothiazepine-7-ol 1,1-dioxide Chromatography of the reaction from Synthetic Example 7 produced mixtures which were combined and rechromatographed using toluene and toluene: EtOAc (95:5) as the eluants, to afford the title product (0.29 g) as a white solid, mp 155–156° C.

Analysis: Calcd: C 65.48; H 7.24; N 3.47; S 7.95; Found: C 65.58; H 7.28; N 3.43; S 8.03; $^1$H NMR (DMSO-d$_6$), δ: 0.76 (3H, t); 0.81 (3H, t); 1.18–2.04 (8H, m); 3.28 (2H,q); 3.82 (3H, s); 5.85 (1H, d); 6.09 (1H, s); 7.31–7.45 (6H, m); 9.43 (1H, s)

SYNTHETIC EXAMPLE 9

Preparation of (3R,5R)-3-Butyl-3-ethyl-2,3,4,5-tetrahydro-7-methoxy-5-phenyl-1,4-benzothiazepine-8-ol 1,1-dioxide Chromatography of the reaction mixtures from Synthetic Example 7 produced the title compounds of Synthetic examples 7 and 8. One other product was also isolated during the chromatography used in Synthetic Example 8. The title product (0.35 g) was isolated as a white solid, mp 165–166° C.

Analysis: Calcd: C 65.48; H 7.24; N 3.47; S 7.95; Found: C 65.32; H 7.28; N 3.49; S 8.00; $^1$H NMR (DMSO-d$_6$), δ: 0.77 (3H, t); 0.81 (3H, t); 1.11–2.08 (8H, m); 3.29 (2H, q); 3.44 (3H, s); 5.86 (1H, d); 6.06 (1H, s); 7.32–7.43 (6H, m); 9.73 (1H, s)

SYNTHETIC EXAMPLE 10

Preparation of (+–)-trans-3-butyl-3-ethyl-2,3,4,5-tetrahydro-8-methoxy-5-phenl-1,4-benzothiazepine 1,1-dioxide (a) O-(2-benzoyl-5-methoxyphenal)dimethylthiocarbamate Sodium hydride (8.8 g, Aldrich) was added slowly to a solution of 2-hydroxy-4-methoxybenzophenone (50.0 g Aldrich) in 300 ml of dimethylformamide. Hexamethylphosphoramide (43.0 g) was then added dropwise and stirred at room temperature for 2 hours. Dimethylthiocarbamoyl chloride (37.0 g Aldrich) was added and stirred overnight at 50° C. The reaction mixture was poured into deionized water (300 mL) and extracted with a petroleum ether/chloroform (1:4) mixture. The organic layer was washed with 10% sodium hydroxide, brine and concentrated to give the title product as a yellow solid (40.0 g). $^1$H NMR was consistent with proposed structure.

(b) S-(2-Benzoyl-5-methoxyphenyl) dimethylthiocarbamate

The product (97.4 g) from step (a) was suspended in tetradecane (500 mL) and heated to an internal temperature of 255° C. for 30 minutes. After cooling to room temperature, the reaction mixture was chromatographed on silica gel using hexane, then hexanes/ethyl acetate (7:3) as eluants to afford the title product (65.0 g) as a tan solid, mp 95–97° C. $^1$H NMR was consistent with proposed structure.

(c) 2-Mercapto-4-methoxybenzophenone

Potassium hydroxide pellets (20.0 g) were slowly added to a solution of the product (28.0 g) from step (b) dissolved in 800 ml methanol/tetrahydrofuran (1:1). After refluxing for 4 hours, the reaction was cooled to room temperature, methylene chloride was added and the solution was extracted with 5% hydrochloric acid. The organic layer was dried and concentrated. Chromatography on silica gel using hexanes/ethyl acetate (99:1) as the eluant afforded the title product as an orange oil (17.1 g). $^1$H NMR consistent with proposed structure.

(d) Ethyl 2-aminobutyrate hydrochloride

A slurry of 2-aminobutyric acid (100 g Aldrich) in absolute ethanol (300 ml) was stirred under nitrogen at 0° C. and thionyl chloride (120.8 g) was added dropwise. The reaction was stirred overnight at 0° C. and then gradually warmed to room temperature. The resulting white slurry was heated under reflux for 3 hours, left to cool for 10 minutes, then poured into chilled diethyl ether (600 ml) with hand stirring. The suspension was filtered and the solid product dried to give the desired product (150 g) as a white solid. $^1$H NMR consistent with proposed structure.

(e) Ethyl 2-benzylideneaminobutyrate

A solution of the product from step (d) (149.6 g), magnesium sulphate (74.3 g), and triethylamine (246 ml) in dichloromethane (1500 ml) was stirred at room temperature under nitrogen and benzaldehyde (94.9 g, Aldrich) was added dropwise. The mixture was stirred at room temperature for 3 hours then filtered. The filtrate was concentrated, triturated in diethyl ether, filtered and concentrated to yield the desired product as a yellow oil (174 g). $^1$H NMR consistent with the proposed structure.

(f) (+–)-Ethyl 2-benzylideneamino-2-ethylhexanoate

Sodium hydride (32.5 g, 60% dispersion in oil) and N,N-dimethylformamide (DMF) (700 ml) were stirred under nitrogen at room temperature and a solution of the product from step (e) (178.1 g) in DMF was added dropwise. After 2 hours stirring at room temperature, a solution of butyl iodide (149.5 g) in DMF was added dropwise and the reaction left stirring for a further 2 hours. The reaction was poured into an ice cold mixture of water (560 ml), diethyl ether (300 ml) and ammonium chloride (120 g). The resulting organic layer was dried over potassium carbonate then concentrated to give the desired product as a brown oil (220 g).

(g) (+−)-Ethyl 2-amino-2-ethylhexanoate

The product from step (f) (233.0 g), was partitioned between petroleum ether and 10% w/w hydrochloric acid (421 ml) and stirred at room temperature for 2 hours. The aqueous layer was extracted twice with petroleum ether and then chilled with ethyl acetate in an ice-salt bath. Sodium hydroxide pellets were added to the mixture until the aqueous layer was at pH 10. The latter was extracted twice with ethyl acetate and the combined ethyl acetate layers were dried over potassium carbonate, then concentrated and vacuum distilled to give the desired product as a colourless oil. $^1$H NMR consistent with the proposed structure.

(h) (+−)-2-Amino-2-ethylhexan-1-ol

Lithium aluminium hydride (22.2 g) was added to anhydrous diethyl ether (450 ml) under nitrogen. The product from step (g) (129.0 g) was diluted with diethyl ether (40 ml) and added dropwise. The reaction was refluxed for 1 hour then cooled to room temperature. 1M sodium hydroxide (23 ml) was added dropwise followed by deionised water. The resulting suspension was filtered and the filtrate concentrated to give the desired product as a colourless oil (87.9 g). $^1$H NMR consistent with the proposed structure.

(i) (+−)-2-Butyl-2-ethylaziridine

Acetonitrile (150 ml) and the product from step (h) (20.0 g) were mixed under nitrogen, cooled to 2–3° C. and chlorosulphonic acid (16.0 g, Aldrich) was added dropwise keeping the temperature below 10° C. The coolant was removed and the slurry left to stir for 80 minutes at room temperature. The reaction was concentrated in vacuo and co-distilled with water (50 ml). 50% Aqueous sodium hydroxide (55.2 g) and water (50 ml) were added and the mixture was distilled at atmospheric pressure. The organic layer was collected from the distillate and dried with solid potassium hydroxide to give the desired product (12.8 g). $^1$H NMR consistent with proposed structure.

(j) (+−)-3-Butyl-3-ethyl-8-methoxy-5-phenyl-2,3-dihydrobenzothiazepine

The product (55.2 g) from step (i), in 2,6-lutidine (100 ml), was added to a solution of the product (118.5 g) from step (c) in 2,6-lutidine (400 ml). The reaction mixture was stirred for 1 hour and p-toluenesulfonic acid (9.0 g) was added and then refluxed with a Dean Stark trap for 17 hours. The reaction mixture was concentrated in vacuo and the residue was partitioned between 5% NaHCO$_3$ and EtOAc. The organic layer was separated, dried and concentrated to get an oil which was chromatographed on silica gel, using hexane: EtOAc (85:15) as the eluant, to afford the title product (124.3 g) as an orange oil. $^1$H NMR consistent with the desired structure.

(k) (+−)-Trans-3-butyl-3-ethyl-2,3,4,5-tetrahydro-8-methoxy-5-phenyl-1,4-benzothiazepine A 1M solution of diborane (40 ml) in THF was added to a solution of the product (12.3 g) from step (j) in THF (150 ml). The reaction mixture was stirred at room temperature for 17 hours, then 6N HCl (50 ml) was added and the solution was concentrated in vacuo. The residue was basified with 50% NaOH and extracted with EtOAc. The EtOAc layer was separated, dried and concentrated in vacuo to give an oil which was chromatographed on silica gel, using hexanes then toluene as the eluants to afford the desired product (4.9 g) as a yellow oil. $^1$H NMR consistent with the desired structure.

(l) (+−)-Trans-3-butyl-3-ethyl-2,3,4,5-tetrahydro-8-methoxy-5-phenyl-1,4-benzothiazepine 1,1-dioxide A solution of the product (4.9 g) from step (k) in trifluoroacetic acid (50 ml) was added to 30% H$_2$O$_2$ in trifluoroacetic acid (50 ml). The reaction mixture was stirred at room temperature for 17 hours, then poured into deionized water (200 ml) followed by the addition of NaOH pellets until a pH of 14 was obtained. The reaction mixture was warmed, at 45° C., for 3 hours then extracted with dichloromethane. The organic layer was separated, dried and concentrated to give an oil which was chromatographed on silica gel, using hexane: EtOAc (9:1) as the eluant, to give the title product as a white solid, mp 123–125° C.

Analysis: Calcd: C 68.18; H 7.54; N 3.61; S 8.27; Found: C 68.19; H 7.49; N 3.55; S 8.35; $^1$H NMR (DMSO-d$_6$), δ: 0.73–0.85 (6H, m, CH$_3$); 1.07–1.47 (4H, m, CH$_2$); 1.48–2.20 (4H, m, CH$_2$); 2.48–2.53 (1H, d, NH); 3.51 (2H, q, CH$_2$SO$_2$); 3.84 (3H, s, OMe); 5.90 (1H, d, CHPh); 6.50 (1H, d, ArH); 7.09–7.20 (1H, m, ArH); 7.32–7.48 (6H, m, ArH)

SYNTHETIC EXAMPLE 11

Preparation of (+−)-trans-3-butyl-3-ethyl-2,3,4,5-tetrahydro-5-phenyl-1,4-benzothiazepine-8-ol 1,1-dioxide This compound was prepared following the procedure of Synthetic Example 7, using the product (4.8 g) from Synthetic Example 10(1). Chromatography on silica gel, using hexane: EtOAc (4:1) as the eluant, gave the title product (1.8 g) as a white solid, mp 130–132° C.

Analysis:Calcd: C67.53; H 7.28; N 3.75; S 8.58; Found: C 67.26; H 7.21; N 3.76; S 8.65; $^1$H NMR (DMSO-d$_6$), δ: 0.70–0.86 (6H, m); 0.96–1.23 (4H, m); 1.25–1.49 (1H, m); 1.66–1.75 (1H, m); 1.98–2.07 (1H, m); 2.40 (1H, d); 3.33 (2H, q); 5.82 (1H, d); 6.35 (1H, d); 6.77–6.80 (1H, m); 7.24–7.38 (6H, m); 10.0 (1H, s)

SYNTHETIC EXAMPLE 12

Preparation of (+−)-trans-3-butyl-3-ethyl-2,3,4,5-tetrahydro-5-phenyl-1,4-benzothiazepine-4,8-diol 1,1-dioxide The product (1.0 g) from Synthetic Example 11 was dissolved in methylene chloride (100 ml), cooled to 0° C. and m-chloroperbenzoic acid (0.55 g, 57–86%, Aldrich) was added. The reaction mixture was stirred at ice bath temperatures for 5 hours then 5% NaHCO$_3$ was added to neutralize excess acid. The organic layer was separated, dried and concentrated in vacuo. The resulting residue was chromatographed on silica gel, using hexane: EtOAc as the eluant, to afford the title product (0.68 g) as a pale yellow solid, mp 213–214° C.

Analysis: Calcd: C 64.76; H 6.99; N 3.60; S 8.23; Found: C 64.86; H 7.03; N 3.63; S 8.31; $^1$H NMR (DMSO-d$_6$), δ: 0.77–0.89 (6H, m); 1.09–1.64 (6H, m); 1.68–2.03 (2H, m); 3.36 (2H, q); 6.30 (1H, s); 6.44 (1H, d); 6.82–6.87 (1H, m); 7.27–7.49 (6H, m); 7.89 (1H, s); 10.0 (1H, s)

SYNTHETIC EXAMPLE 13

Preparation of (+−)-Trans-3-butyl-3-ethyl-2,3,4,5-tetrahydro-8-methyl-5-phenyl-1,4-benzothiazepine 1,1-dioxide (a) 3-Methylphenyl benzoate A solution of benzoyl chloride (32.5 g, Aldrich) in ether (200 ml) was added dropwise to a stirred solution of m-cresol (25.0 g, Aldrich) and triethylamine (27.2 g, Aldrich) in ether (500 ml). The reaction mixture was stirred at room temperature for 1 hour then filtered. The ethereal filtrate was washed with saturated NaHCO$_3$ and water then dried over Na$_2$SO$_4$. The ether layer was separated, dried and concentrated in vacuo to give the desired product (104.0 g) as a white solid, mp 45–47C. $^1$H NMR consistent with the desired structure.

(b) 2-Hydroxy-4-methylbenzophenone

The product (48 g) from step (a) was melted (at 70° C.) and aluminum chloride (30.2 g) was added in portions. The reaction mixture was heated to 200° C. for 5 minutes, then cooled to room temperature. The resulting solid was ground to a powder and slowly added to a mixture of conc. HCl (800 ml) and ice. This mixture was extracted with ether and the ether was washed with water. The ether layer was separated, dried and concentrated. The resulting residue was chromatographed on silica gel, using toluene as the eluant, to afford the title product (39 g) as a yellow oil. $^1$H NMR consistent with the desired structure.

(c) (+−)-Trans-3-butyl-3-ethyl-2,3,4,5-tetrahydro-8-methyl-5-phenyl-1,4-benzothiazepine 1,1-dioxide The product from step (b) was converted to the title product following the procedures used in steps (a) to (l) of Synthetic Example 10. The title product was isolated as a white solid, mp 121–122° C.

Analysis: C 71.12; H 7.87; N 3.77; S 8.63; Found: C 71.23; H 7.94; N 3.67; S 8.74; $^1$H NMR (DMSO-d$_6$); δ: 0.77–0.82 (6H, m); 1.16–2.07 (8H, m); 2.36 (3H, s); 3.37 (2H, q); 5.92 (1H, d); 6.47 (1H, d); 7.27–7.39 (6H, m); 7.79 (1H, s)

SYNTHETIC EXAMPLE 14

Preparation of (+−)-Trans-3-butyl-3-ethyl-2,3,4,5-tetrahydro-8-methoxy-5-phenyl-1,4-benzothiazepine-7-carbaldehyde 1,1-dioxide (a) (+−)-7-Bromo-3-butyl-3-ethyl-2,3-dihydro-8-methoxy-5-phenyl-1,4-benzothiazepine 2,3-Dichloro-5,6-dicyano-1,4-benzoquinone(16.9 g) was added directly to a benzene solution(300 ml) of the product (as the racemate)(30.2 g) from Synthetic Example 5 (g). The reaction mixture was stirred at reflux for 3 hours, cooled to room temperature. 1N NaOH(200 ml) was added, stirred for 30 minutes; then the organic layer was separated, washed with brine and 1N NaOH. The benzene layer was separated, dried and concentrated to get an oil which was solubilized in hexane, filtered and concentrated to get the title product (25.8 g) as a red oil. $^1$H NMR consistent with the desired structure.

(b) (+−)-3-Butyl-7-carbaldehyde-3-ethyl-2,3-dihdro-8-methoxy-5-phenyl-1,4-benzothiazepine A solution of 1.6M n-butyl lithium (49.0 ml) was to an ice-cooled solution of the product(25.8 g) from step (a) in hexane (500 ml). The reaction mixture was stirred for 25 minutes and 4-formylmorpholine(9.0 g). The ice bath was removed and the reaction was stirred at room temperature for 2½ hours. The reaction was quenched with a saturated solution (250 ml) of NH$_4$Cl and stirred for 60 minutes. The organic layer was separated, dried and concentrated to get 26.9 g of a red oil. Chromatography on silica gel, using hexane:EtOAc(85:15) as eluant afforded the title product (13.9 g) as an orange oil. $^1$H NMR consistent with the desired structure.

(c) (+−)-Trans-3-butyl-3-ethyl-2,3,4,5-tetrahydro-8-metho-5-phenyl-1,4-benzothiazepine-7-carbaldehyde Ethylene glycol(9.3 g) and pyridinium p-toluenesulfonate (1.3 g) were added to a benzene solution (250 ml) of the product(19.0 g) from step (b) and this mixture was refluxed in a Dean Stark trap for 17 hours. The reaction mixture was cooled to room temperature and treated with aqueous NaHCO$_3$ (150 ml) for 15 minutes. The organic layer was separated, dried and concentrated to get a thick yellow-orange oil(19.7 g). $^1$H nmr was consistent for the dioxolane derivative. This oil was then treated with B$_2$H$_6$, following the procedure cited in Synthetic Example 1 (n), to give the title product(3.5 g) as an orange oil. $^1$H NMR consistent with the desired structure.

(d) (+−)-Trans-3-butyl-3-ethyl-2,3,4,5-tetrahydro-8-methoxy-5-phenyl-1,4-benzothiazepine-7-carbaldehyde 1,1-dioxide The product(3.5 g) from step (c) was dissolved in t-butanol/THF (1:4, 60 ml) and N-methylmorpholine N-oxide(3.4 g) was added, followed by 2.5 wt. % of OsO$_4$ in 2-methyl-2-propanol (5.0 ml). The reaction mixture was stirred at room temperature ofr 17 hours then diluted with EtOAc (250 ml). The organic layer was separated, washed with 1N NaOH (2×50 ml) and brine. The organic layer was separated, dried and concentrated to give an oil which upon trituration in diethyl ether afforded the title product (3.10 g) as a white solid, mp 127–128° C.

Analysis: Calcd: C 66.48; H 7.03; N 3.37; S 7.72; Found: C 66.26; H 7.04; N 3.30; S 7.82; $^1$H NMR(DMSO-d$_6$), δ: 0.73–0.86(6H, m); 1.07–2.05(8H, m); 2.65(1H, d); 3.50(2H, q); 4.03(3H, s); 5.91(1H, s); 6.92(1H, s); 7.33–7.48(5H, m); 7.74(1H, s); 10.28(1H, s)

SYNTHETIC EXAMPLE 15

Preparation of (+−)-Trans-2-((3-butyl-3-ethyl-2,3,4,5-tetrahydro-8-methoxy-5-phenyl-1,4-benzothiazepine-7-yl)methoxy) ethanol S,S-dioxide Chromatography of the reaction from Synthetic Example 14 (c) afforded the corresponding sulfide compound(2.3 g) of the title product as an oil. $^1$H NMR was consistent for the desired structure. This oil was then treated, according to the procedure shown in Synthetic Example 1 (o), to yield the title product (0.65 g) as a white solid, mp 83–850° C.

Analysis: Calcd: C 65.05; H 7.64; N 3.03; S 6.95; Found: C 64.82; H 7.72; N 2.99; S 6.91; $^1$H NMR(DMSO-d6), δ: 0.74–0.86(6H, m); 1.07–2.14(8H, m); 2.52(1H, d); 3.35(4H, m); 3.41(2H, q); 3.87(3H, s); 4.39(2H, s); 4.54(1H, t); 5.91(1H, d,); 6.64(1H, s); 7.29–7.45(5H, m); 7.51(1H, s)

SYNTHETIC EXAMPLE 16

Preparation of (+−)-Trans-3-butyl-3-ethyl-2,3,4,5-tetrahydro-8-hydroxy-5-phenyl-1,4-benzothiazepine-7-carbaldehyde 1,1-dioxide The product (2.0 g) from Synthetic Example 14 (d) was added to glacial acetic acid (20 ml) and 48% HBr (20 ml)) and heated to 150° C. for 24 hours. The reaction mixture was concentrated in vacuo, partitioned between diethyl ether and 5% NaHCO$_3$. The organic layer was separated, dried and concentrated to give the title product (0.85 g) as a tan solid, mp 158–159° C.

Analysis: Calcd: C 65.81; H 6.78; N 3.49, S 7.99; Found: C 65.63; H 7.04; N 3.32; S 7.74; $^1$H NMR(DMSO-d$_6$), δ: 0.72–0.85(6H, m); 1.07–2.05(8H, m); 2.58(1H, d); 3.46(2H, q); 5.85(1H, d); 6.83(1H, s); 7.34–7.47(5H, m); 7.70(1H, s); 10.25(1H, s); 11.33(1H, broad s)

SYNTHETIC EXAMPLE 17

Preparation of (+−)-Trans-3-butyl-3-ethyl-2,3,4,5-tetrahydro-5-phenyl-1,4-benzothiazepine-8-thiol 1,1-dioxide The product from Synthetic Example 11 was treated according to the procedures shown in Synthetic Example 1 (i)–(k) to give the title product as a white solid, mp 108–110° C.

Analysis: Calcd: C 64.75; H 6.99; N 3.60; S 16.46; Found: C 64.83; H 7.03; N 3.56; S 16.54; $^1$H NMR(DMSO-d$_6$), δ: 0.70–0.81(6H, m); 1.05–2.06(8H, m); 2.54(1H, d); 3.37(2H, q); 5.85(1H, d); 6.06(1H, broad s); 6.40(1H, d); 7.26–7.40 (6H, m); 7.90(1H, s)

SYNTHETIC EXAMPLE 18

Preparation of (+−)-Trans-3-butyl-3-ethyl-2,3,4,5-tetrahydro-5-phenyl-1,4-benzothiazepine-8-sulfonic acid 1,1-dioxide The product(5.3 g) from Synthetic Example 17 was dissolved in DMSO (13 ml). Water (0.3 ml)and 48% HBr (0.2 ml) were then added. The reaction mixture was heated to 120° C., allowing for distillate to be removed, for a period of 4 hours. The reaction mixture was cooled to room temperature, diluted with 1N NaOH, and filtered through a sintered glass funnel. The filtrate was acidified with 1N HCl, the resulting solids were filtered and dried to get the title product(1.6 g) as a beige solid, mp>295° C.

Analysis: Calcd. C 57.64; H 6.22; N 3.20; S 14.65; Found: C 57.48; H 6.19; N 3.25; S 14.73; $^1$H NMR (DMSO-d$_6$), S: 0.82–0.95(6H, m); 1.32–2.06(8H, m); 2.54(1H, d); 3.93(2H, q); 4.70(1H, broad s); 6.23(1H, s); 6.93(1H, d); 7.60(6H, broad s); 7.84(1H, d); 8.30(1H, s)

SYNTHETIC EXAMPLE 19

Preparation of (7R,9R)-7-Butyl-7-ethyl-6,7,8,9-tetrahydro-9-phenyl-1,3-dioxolo(4,5-H)(1,4)-benzothiazepine 5,5-dioxide The product(0.74 g) from Synthetic Example 7 was dissolved in DMF (5 ml). Potassium carbonate(0.50 g) and bromochloroethane(0.47 g) were added to the reaction mixture and stirred at 110° C. for 2 hours. The mixture was filtered through Celite, washed with EtOAc, and the filtrate was dried and concentrated to get an oil. Chromatography on silica gel, using hexane:EtOAc(1:1) as eluant, afforded the title product(0.68 g) as a white solid, mp 71–73° C.

Analysis: Calcd. C 65.81; H 6.78; N 3.49; S 7.99; Found: C 65.89; H 6.80; N 3.50; S 8.08; $^1$H NMR(DMSO-d$_6$), δ: 0.71–0.85(6H, m); 1.05–2.12(8H, m); 2.49(1H, d); 3.25(2H, q); 3.42(2H, s); 5.91(1H, d); 6.06(1H, s);7.27–7.41(6H, m)

SYNTHETIC EXAMPLE 20

Preparation of (+−)-Trans-3-butyl-3-ethyl-2,3,4,5-tetrahydro-8.9-dimethoxy-5-phenyl-1,4-benzothiazepine 1,1-dioxide (a) 2-Hydroxy-3,4-methoxybenzaldehyde Aluminum chloride(21.8 g) was added, spatula-wise, to an ice-chilled solution of benzoyl chloride(22.1 g) and 1,2,3-trimethoxybenzene(25.0 g) in 1,2-dichloroethane (250 ml). The reaction mixture was stirred at 0–5° C. for 3 hours, then heated to reflux for 2 hours. The reaction mixture was then poured onto ice/concentrated HCl (100 ml) and stirred for 30 minutes, then extracted with diethyl ether. The organic layer was separated, dried and concentrated to get a solid(23.0 g). Chromatography on silica gel , using toluene:EtOAc(9:1) as eluant, afforded the title product(18.0 g) as a white solid, mp 127–128°C. 1H NMR consistent with the desired structure.

(b) (+−)-Trans-3-butyl-3-ethyl-2,3,4,5-tetrahydro-8,9-dimethoxy-5-phenyl-1,4-benzothiazepine 1,1-dioxide The product from step (a) was converted to the title product following the procedures used in steps (a) to (l) of Synthetic Example 10. The title product was isolated as a white solid, mp 142–144° C.

Analysis: C 66.16; H 7.48; N 3.35; S 7.68; Found: C 66.03; H 7.53; N 3.28; S 7.77; $^1$H NMR(DMSO-d$_6$), δ: 0.64(3H, t); 0.81(3H, t); 0.87–2.08(8H, m); 2.42(1H, d); 3.73(2H, q); 3.75(3H, s); 3.79(3H, s); 5.50(1H, d); 6.05(1H, d); 6.97(1H, d); 7.27–7.41(5H, m)

SYNTHETIC EXAMPLE 21

Preparation of (3R,5R)-3-butyl-3-ethyl-5-(4-fluorophenyl)-2,3,4,5-tetrahydro-7,8-dimethoxy-1,4-benzothiazpin-4-ol 1,1-dioxide (a) 2-Hydroxy-4,5-Dimethoxy-4'-fluorobenzophenone A 1.0M solution of boron trichloride(142 ml) in dichloromethane was added to 4-fluorobenzoyl chloride (16.8 ml) in benzene (200 ml). Next, 3,4-dimethoxyphenol (20.0 g) in benzene (100 ml) was added and the reaction mixture was stirred at room temperature for 2 hours. The mixture was then poured onto ice water and allowed to stir for 15 minutes, then 1N HCl (500 ml) was added and stirred at room temperature for 17 hours. The reaction mixture was extracted with EtOAc, the EtOAc was separated, concentrated and dried to give the title product(41.7 g) as an orange solid. $^1$H NMR consistent with desired structures.

(b) (3R,5R)-3-buty-3-ethyl-5-(4-fluorophenyl)-2,3,4,5-tetrahydro-7,8-dimethoxy-1,4-benzothiazpin-4-ol 1,1-dioxide The product from step (a) was converted to the title product following the procedures used in steps (a) to (o) of Synthetic Example 1 and the procedure used in Synthetic Example 2. The title product was isolated as white solid, mp 170–171° C.

Analysis: C 61.18; H 6.70; N 3.10; S 7.10; Found: C 61.28; H 6.78; N 2.99; S 7.27; $^1$H NMR(DMSO-d$_6$), δ: 0.75–0.85(6H, m); 1.07–2.04(8H, m); 3.35(2H, q); 3.42(3H, s); 3.81(3H, s); 6.07(1H, s); 6.33(1H, s); 7.22(2H, t); 7.39 (1H, s); 7.40–7.50(2H, m); 7.96(1H, s)

SYNTHETIC EXAMPLES 22–54

Each of the following examples was prepared by a method analagous to that of Synthetic Example 1, by one of the other exemplified routes or by chemical methods known to those in the art. In all cases, $^1$H NMR and elemental analysis were consistent with the proposed structure.

(22) (+−)-Trans-3-butyl-3-ethyl-2,3,4,5-tetrahydro-8-methoxy-5-phenyl 1,4-benzothiazepine-7-methanol S,S-dioxide, mp 122–123° C.

(23) (3R,5R)-3-butyl-3-ethyl-2,3,4,5-tetrahydro-8-methoxy-7-nitro-5-phenyl-1,4-benzothiazepine 1,1-dioxide 0.40 hydrate, mp 122–123° C.

(24) (+−)-Trans-3-butyl-3-ethyl-2,3,4,5-tetrahydro-8-methoxy-7-(methoxymethyl)-5-phenyl-1,4-benzothiazepine 1,1-dioxide, mp 118–119° C.

(25) (+−)-Trans-7-bromo-3-butyl-3-ethyl-2,3,4,5-tetrahydro-5-phenyl-1,4-benzothiazepin-8-ol 1,1-dioxide 0.40 hydrate, mp 137–138° C.

(26) (+−)-Trans-3-butyl-3-ethyl-2,3,4,5-tetrahydro-7,8,9-trimethoxy-5-phenyl-1,4-benzothiazepine 1,1-dioxide, mp 169–170° C.

(27) (3R,5R)-3-butyl-3-ethyl-2,3,4,5-tetrahydro-5-phenyl-1,4-benzothiazepin-7,8-diyl diacetate 1,1-dioxide, mp 79–81° C.

(28) (8R,10R)-8-Butyl-8-ethyl-2,3,7,8,9,10-hexahydro-10-1,4-dioxono(2,3-H)(1,4)-benzothiazepine 6,6-dioxide, mp 82° C.

(29) (3R,5R)-3-butyl-7,8-diethoxy-2,3,4,5-tetrahydro-5-phenyl-1,4-benzothiazepine 1,1 dioxide 0.20 hydrate, mp 110–111° C.

(30) (+−)-Trans-3-butyl-8-ethoxy-3-ethyl-2,3,4,5-tetrahydro-5-phenyl-1,4-benzothiazepine 1,1-dioxide, mp 45–54° C.

(31) (+−)-Trans-3-butyl-3-ethyl-2,3,4,5-tetrahydro-8-(methylthio)-5-phenyl-1,4-benzothiazepine1,1-dioxide hydrochloride, mp 194–197° C.

(32) (+−)-Trans-3-butyl-3-ethyl-2,3,4,5-tetrahydro-8-isopropoxy-5-phenyl-1,4-benzothiazepine 1,1-dioxide hydrochloride, mp 178–181° C.

(33) (+−)-Trans-3-butyl-3-ethyl-2,3,4,5-tetrahydro-5-phenyl-1,4-benzothiazepin-8-carbaldehyde 1,1-dioxide, mp 165–170° C.

(34) 3,3-Diethyl-2,3,4,5-tetrahydro-1,1-dioxo-5-phenyl-1,4-benzothiazepin-8-yl aspartate

(35) 3,3-Diethyl-2,3,4,5-tetrahydro-7,8-dimethoxy-5-phenyl-1,4-benzothiazepine-1,1-dioxide, mp 163–164° C.

(36) 3,3-Diethyl-5-(4-fluorophenyl)-2,3,4,5-tetrahydro-8-methoxy-1,4-benzothiazepine-1,1-dioxide mp 101–103° C.

(37) 3,3-Diethyl-2,3,4,5-tetrahydro-8-methoxy-5-phenyl-1,4-benzothiazepine-1,1-dioxide, mp 132–133° C.

(38) 3,3-Diethyl-2,3,4,5-tetrahydro-5-phenyl-1,4-benzothiazepin-4,8-diol-1,1-dioxide, mp 225–227° C.

(39) (RS)-3,3-Diethyl-2,3,4,5-tetrahydro4-hydroxy-7,8-dimethoxy-5-phenyl-1,4-benzothiazepine 1,1-dioxide, mp 205–206° C.

(40) (+−)-Trans-3-butyl-8-ethoxy-3-ethyl-2,3,4,5-tetrahydro-5-phenyl-1,4-benzothiazepin4ol 1,1-dioxide, mp 149–150° C.

(41) (+−)-Trans-3-butyl-3-ethyl-2,3,4,5-tetrahydro-8-isopropoxy-5-phenyl-1,4-benzothazepin-4-ol 1,1-dioxide, mp 109–115° C.

(42) (+−)-Trans-3-butyl-3-ethyl-2,3,4,5-tetrahydro-7,8,9-trimethoxy-5-phenyl-1,4-benzothiazepin-4-ol 1,1-dioxide, mp 84–96° C.

(43) (3R,5R)-3-butyl-3-ethyl-2,3,4,5-tetrahydro-5-phenyl-1,4-benzothiazpin-4,7,8-triol-1,1-dioxide, mp 215–220° C.

(44) (+−)-Trans-3-butyl-3-ethyl-2,3,4,5-tetrahydro-4,7,8-trimethoxy-5phenyl-1,4-benzothiazepine 1,1-dioxide, mp 169–87° C.

(45) (+−)-Trans-3-butyl-3-ethyl-5-phenyl-2,3,4,5-tetrahydro-7,8-dimethoxy-1,4-benzothiazepin-4-yl acetate S,S-dioxide, mp 154–156° C.

(46) 3,3-Diethyl-2,3,4,5-tetrahydro-5-phenyl-1,4-benzothiazepin-8-ol1,1-dioxide, mp 177–178° C.

(47) 3,3-Diethyl-2,3,4,5-tetrahydro-7-methoxy-5-phenyl-1,4-benzothiazepin-8-ol 1,1-dioxide

(48) 3,3-Dibutyl-2,3,4,5-tetrahydro-5-phenyl-1,4-benzothiazepin-8-ol1,1-dioxide

(49) (+−)-Trans-3-Butyl-3-ethyl-2,3,4,5-tetrahydro-1,1-dioxo-5-phenyl-1,4-benzothiazepin-8-yl hydrogen sulfate, mp 196.5–200° C.

(50) (+−)-Trans-3-Butyl-3-ethyl-2,3,4,5-tetrahydro-1,1-dioxo-5-phenyl-1,4-benzothiazepin-8-yl dihydrogen phosphate

(51) 3,3-Diethyl-2,3,4,5-tetrahydro-1,1-dioxo-5-phenyl-1,4-benzothiazepin-8-ylhydrogen sulfate

(52) 3,3-Diethyl-2,3,4,5-tetrahydro-1,1-dioxo-5-phenyl-1,4-benzothiazepin-8-yldihydrogen phosphate

(53) (+−)-Trans-3-Butyl-3-ethyl-2,3,4,5-tetrahydro-1,1-dioxo-5-phenyl-1,4-benzothiazepin-8-yl aspartate Biological Assay In vivo inhibition of bile acid uptake Inhibiting intestinal bile acid absorption with bile acid sequestrants or surgically with partial ileal bypass surgery is an effective way to decrease plasma LDL cholesterol concentration. Another approach to decreasing bile acid absorption is inhibiting the ileal bile acid active uptake transport system. It has been shown that this inhibition, as measured by the fecal excretion of bile acids results in hypocholesterolemic activity. (1) Lewis, M. C.; Brieaddy, L. E.; and Root, C. Effects of 2164U90 on Ileal Bile Acid Absorption and Serum Cholesterol in Rats and Mice. *J. Lipid. Research.*, 1995, 36, 1098–1105.

Fecal Excretion of Bile Acids

Male Sprague-Dawley rats weighing 220–260 g were housed in individual cages and fed normal chow. The rats were divided into 6 treatment groups of 10 to 12 rats per group. The rats were dosed by oral gavage(1 mL/100 g body weight) with test compounds as a suspension in 0.5% methylcellulose at 9:00 am and 3:30 pm for two days. The control group received 0.5% methylcellulose. Two hours after the morning dose on day two, the rats were given a trace amount(1.3 nmoles) of 23, 25-$^{75}$Se-homocholic acid taurine($^{75}$SeHCAT) in 1.0 mL saline orally. $^{75}$SeHCAT, a synthetic gamma emitting bile acid analog which is absorbed by the ileal bile acid uptake system similar to taurocholic acid, has been used clinically as a measure of ileal bile acid absorptionl,[1,2]. Feces were collected over the 24 hr following $^{75}$SeHCAT administration. Fecal content of $^{75}$SeHCAT was determined using a Packard Auto-Gamma 5000 Series gamma-counter. Representative data are tabulated in Table 1 as the % inhibition of $^{75}$SeHCAT.

(1) Galatola, G.; Jazrawi, R. P.; Bridges, C.; Joseph, A. E. A. and Northfield, T. C. Direct Measurement of First-Pass Ileal Clearance of a Bile Acid in Humans. *Gastroenterology.* 1991, 100, 1100–1105.

(2) Ferraris, R.; Galatoa, G.; Barlotta, A; Pellerito, R.; Fracchia, M.; Cottino, F. and De La Pierre, M. Measurement of Bile Acid Half-Life Using [$^{75}$Se]HCAT in Health and Intestinal Diseases. *Dig. Dis. Sci.* 1992, 37, 225–232.

TABLE 1

| Compound of | (% Inhibition of $^{75}$SeHCAT) Dose (mg/kg) | | |
|---|---|---|---|
| Example | 1.0 | 0.3 | 0.1 |
| 1 | | 51 | 54 |
| 7 | | 65 | 72 |
| 9 | | 80 | 70 |
| 10 | | 53 | 33 |
| 11 | | 72 | 71 |
| 14 | 56 | 41 | |
| 16 | 44 | 34 | |
| 18 | 39 | 12 | |
| 24 | 49 | 24 | |
| 45 | 26 | 6 | |

In comparison, the most active compound specifically disclosed in International Patent Application No. WO 93/16055 produced a 9% inhibition of $^{75}$SeHCAT at 1.0 mg/kg in this assay.

Pharmaceutical Composition Examples

In the following Examples, the active compound can be any compound of formula (I) and/or a pharmaceutically acceptable salt, solvate, or physiologically finctional derivative thereof. The active compound is preferably (3R,5R)-3-butyl-3-ethyl-2,3,4,5-tetrahydro-7,8-dimethoxy-5-phenyl-1-4-benzothiazepine 1,1-dioxide or one of the compounds of Synthetic Examples 2 to 53.

(i) Tablet compositions

The following compositions A and B can be prepared by wet granulation of ingredients (a) to (c) and (a) to (d) with a solution of povidone, followed by addition of the magnesium stearate and compression.

Composition A

|     |                        | mg/tablet | mg/tablet |
| --- | ---------------------- | --------- | --------- |
| (a) | Active ingredient      | 250       | 250       |
| (b) | Lactose B.P.           | 210       | 26        |
| (c) | Sodium Starch Glycollate | 20      | 12        |
| (d) | Povidone B.P.          | 15        | 9         |
| (e) | Magnesium Stearate     | 5         | 3         |
|     |                        | 500       | 300       |

Composition B

|     |                        | mg/tablet | mg/tablet |
| --- | ---------------------- | --------- | --------- |
| (a) | Active ingredient      | 250       | 250       |
| (b) | Lactose 150            | 150       | —         |
| (c) | Avicel PH 101          | 60        | 26        |
| (d) | Sodium Starch Glycollate | 20      | 12        |
| (e) | Povidone B.P.          | 15        | 9         |
| (f) | Magnesium Stearate     | 5         | 3         |
|     |                        | 500       | 300       |

Composition C

|                        | mg/tablet |
| ---------------------- | --------- |
| Active ingredient      | 100       |
| Lactose                | 200       |
| Starch                 | 50        |
| Povidone               | 5         |
| Magnesium Stearate     | 4         |
|                        | 359       |

The following compositions D and E can be prepared by direct compression of the admixed ingredients. The lactose used in composition E is of the direct compression type.

Composition D

|                        | mg/tablet |
| ---------------------- | --------- |
| Active ingredient      | 250       |
| Magnesium Stearate     | 4         |
| Pregelatinised Starch NF15 | 146   |
|                        | 400       |

Composition E

|                        | mg/tablet |
| ---------------------- | --------- |
| Active ingredient      | 250       |
| Magnesium Stearate     | 5         |
| Lactose                | 145       |
| Avicel                 | 100       |
|                        | 500       |

Composition F (Controlled release composition)

|     |                        | mg/tablet |
| --- | ---------------------- | --------- |
| (a) | Active ingredient      | 500       |
| (b) | Hydroxypropylmethylcellulose (Methocel K4M Premium) | 112 |
| (c) | Lactose B.P.           | 53        |
| (d) | Povidone B.P.C.        | 28        |
| (e) | Magnesium Stearate     | 7         |
|     |                        | 700       |

The composition can be prepared by wet granulation of ingredients (a) to (c) with a solution of povidone, followed by addition of the magnesium stearate and compression.

Composition G (Enteric-coated tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated controlled release tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule compositions

Composition A

Capsules can be prepared by admixing the ingredients of Composition D above and filling two-part hard gelatin capsules with the resulting mixture. Composition B (jnfa) may be prepared in a similar manner.

Composition B

|     |                        | mg/capsule |
| --- | ---------------------- | ---------- |
| (a) | Active ingredient      | 250        |
| (b) | Lactose B.P.           | 143        |
| (c) | Sodium Starch Glycollate | 25       |
| (d) | Magnesium Stearate     | 2          |
|     |                        | 420        |

Composition C

|     |                        | mg/capsule |
| --- | ---------------------- | ---------- |
| (a) | Active ingredient      | 250        |
| (b) | Macrogol 4000 BP       | 350        |
|     |                        | 600        |

Capsules can be prepared by melting the Macrogol 4000 BP, dispersing the active ingredient in the melt and filling two-part hard gelatin capsules therewith.

Composition D

|   | mg/capsule |
|---|---|
| Active ingredient | 250 |
| Lecithin | 100 |
| Arachis Oil | 100 |
|   | 450 |

Capsules can be prepared by dispersing the active ingredient in the lecithin and arachis oil and filling soft, elastic gelatin capsules with the dispersion.

Composition E (Controlled release capsule)

|   |   | mg/capsule |
|---|---|---|
| (a) | Active ingredient | 250 |
| (b) | Microcrystalline Cellulose | 125 |
| (c) | Lactose BP | 125 |
| (d) | Ethyl Cellulose | 13 |
|   |   | 513 |

The controlled release capsule composition can be prepared by extruding mixed ingredients (a) to (c) using an extruder, then spheronising and drying the extrudate. The dried pellets are coated with a release controlling membrane (d) and filled into two-part, hard gelatin capsules.

Composition F (Enteric capsule)

|   |   | mg/capsule |
|---|---|---|
| (a) | Active ingredient | 250 |
| (b) | Microcrystalline Cellulose | 125 |
| (c) | Lactose BP | 125 |
| (d) | Cellulose Acetate Phthalate | 50 |
| (e) | Diethyl Phthalate | 5 |
|   |   | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated controlled release capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(iii) Intravenous injection composition

| Active ingredient | 0.200 g |
|---|---|
| Sterile, pyrogen-free phosphate buffer (pH 9.0) to | 10 ml |

The active ingredient is dissolved in most of the phosphate buffer at 35–40° C., then made up to volume and filtered through a sterile micropore filter into sterile 10 ml ylass vials (Type 1) which are sealed with sterile closures and overseals.

(iv) Intramuscular injection composition

| Active ingredient | 0.20 g |
|---|---|
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml ylass vials (Type 1).

(v) Syrup composition

| Active ingredient | 0.25 | g |
|---|---|---|
| Sorbitol Solution | 1.50 | g |
| Glycerol | 1.00 | g |
| Sodium Benzoate | 0.005 | g |
| Flavour | 0.0125 | ml |
| Purified Water q.s. to | 5.0 | ml |

The sodium benzoate is dissolved in a portion of the purified water and the sorbitol solution added. The active ingredient is added and dissolved. The resulting solution is mixed with the glycerol and then made up to the required volume with the purified water.

(vi) Suppository composition

|   | mg/suppository |
|---|---|
| Active ingredient | 250 |
| Hard Fat, BP (Witepsol H15-Dynamit NoBel) | 1770 |
|   | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38–40° C., 2.02 g aliquots of the mixture are filled into suitable plastic moulds and the suppositories allowed to cool to room temperature.

(vii) Pessarv composition

|   | mg/pessary |
|---|---|
| Active ingredient (63 lm) | 250 |
| Anhydrous Dextrose | 380 |
| Potato Starch | 363 |
| Magnesium Stearate | 7 |
|   | 1000 |

The above ingredients are mixed directly and pessaries prepared by compression of the resulting mixure.

(viii) Transdermal composition

| Active ingredient | 200 mg |
|---|---|
| Alcohol USP | 0.1 ml |
| Hydroxyethyl cellulose |   |

The active ingredient and alcohol USP are gelled with hydroxyethyl cellulose and packed in a transdermal device with a surface area of 10 cm².

I claim:
1. The compounds of the formula (IVa)

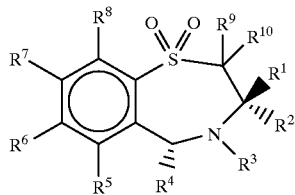

(IVa)

wherein
R$^1$ is a straight chained C$_{1-6}$ alkyl group;
R$^2$ is a straight chained C$_{1-6}$ alkyl group;
R$^3$ is hydrogen or a group OR$^{11}$ in which R$^{11}$ is hydrogen, optionally substituted C$_{1-6}$ alkyl or a C$_{1-6}$ alkylcarbonyl group;
R$^4$ is un-substituted phenyl;
R$^5$ is hydrogen;
R$^6$ and R$^8$ are independently selected from hydrogen, C$_{1-4}$ alkyl optionally substituted by fluorine, C$_{1-4}$ alkoxy, halogen, or hydroxy;
R$^7$ is selected from OR$^{15}$, S(O)$_n$R$^{15}$, OCOR$^{15}$, OCF$_3$, OCN, SCN, CHO, OCH$_2$OR$^{15}$, OCH=CHR$^{15}$, O(CH$_2$CH$_2$O)nR$^{15}$, O(CH$_2$)$_p$SO$_3$R$^{15}$, O(CH$_2$)$_p$NR$^{12}$R$^{13}$ and O(CH$_2$)$_p$N$^+$R$^{12}$R$^{13}$R$^{14}$ wherein p is an integer from 1–4, n is an integer from 0–3, and R$^{12}$, R$^{13}$, R$^{14}$, and R$^{15}$ are independently selected from hydrogen and optionally substituted C$_{1-6}$ alkyl;
R$^9$ and R$^{10}$ are the same or different and each is selected from hydrogen or C$_{1-6}$ alkyl; and
salts, solvates and physiologically functional derivatives thereof.

2. A compound selected from the group consisting of:
(3R,5R)-3-Butyl-3-ethyl-2,3,4,5-tetrahydro-7,8-dimethoxy-5-phenyl-1,4-benzothiazepine 1,1-dioxide;
(3R,5R)-3-Butyl-3-ethyl-2,3,4,5-tetrahydro-7,8-dimethoxy-5-phenyl-1,4-benzothiazepin-4-ol 1,1-dioxide;
(+−)-Trans-3-butyl-3-ethyl-2,3,4,5-tetrahydro-7,8-dimethoxy-5-phenyl-1,4-benzothiazepine 1,1-dioxide;
(+−)-Trans-3-butyl-3-ethyl-2,3,4,5-tetrahydro-7,8-dimethoxy-5-phenyl-1,4,-benzothiazepin-4-ol 1,1-dioxide;
(3R,5R)-7-Bromo-3-butyl-3-ethyl-2,3,4,5-tetrahydro-8-methoxy-5-phenyl-1,4-benzothiazepine 1,1-dioxide;
(3R,5R)-7-Bromo-3-butyl-3-ethyl-2,3,4,5-tetrahydro-8-methoxy-5-phenyl-1,4-benzothiazepin-4-ol 1,1-dioxide;
(3R,5R)-3-Butyl-3-ethyl-2,3,4,5-tetrahydro-5-phenyl-1,4-benzothiazepine-7,8-diol 1,1-dioxide;
(3R,5R)-3-Butyl-3-ethyl-2,3,4,5-tetrahydro-8-methoxy-5-phenyl-1,4-benzothiazepin-7-ol 1,1-dioxide;
(3R,5R)-3-Butyl-3-ethyl-2,3,4,5-tetrahydro-7-methoxy-5-phenyl-1,4-benzothiazepin-8-ol 1,1-dioxide;
(+−)-Trans-3-butyl-3-ethyl-2,3,4,5-tetrahydro-8-methoxy-5-phenyl-1,4-benzothiazepine 1,1-dioxide;
(+−)-Trans-3-butyl-3-ethyl-2,3,4,5-tetrahydro-5-phenyl-1,4-benzothiazepin-8-ol 1,1-dioxide;
(+−)-Trans-3-butyl-3-ethyl-2,3,4,5-tetrahydro-5-phenyl-1,4-benzothiazepine-4,8-diol;
(+−)-Trans-3-butyl-3-ethyl-2,3,4,5-tetrahydro-5-phenyl-1,4-benzothiazepin-8-thiol 1,1-dioxide;
(+−)-Trans-3-butyl-3-ethyl-2,3,4,5-tetrahydro-5-phenyl-1,4-benzothiazepin-8-sulfonic acid 1,1-dioxide;
(+−)-Trans-3-butyl-3-ethyl-2,3,4,5-tetrahydro-8,9-dimethoxy-5-phenyl-1,4-benzothiazepine-1,1-dioxide;
(3R,5R)-3-butyl-7,8-diethoxy-2,3,4,5-tetrahydro-5-phenyl-1,4-benzothiazepine 1,1-dioxide;
(+−)-Trans-3-butyl-8-ethoxy-3-ethyl-2,3,4,5-tetrahydro-5-phenyl-1,4-benzothiazepine-1,1-dioxide;
(+−)-Trans-3-buty-3-ethyl-2,3,4,5-tetrahydro-8-isopropoxy-5-phenyl-1,4-benzothiazepine 1,1-dioxide hydrochloride;
(+−)-Trans-3-butyl-3-ethyl-2,3,4,5-tetrahydro-5-phenyl-1,4-benzothiazepin-8-carbaldehyde-1,1-dioxide;
3,3-Diethyl-2,3,4,5-tetrahydro-7,8-dimethoxy-5-phenyl-1,4-benzothiazepine 1,1-dioxide;
3,3-Diethyl-2,3,4,5-tetrahydro-8-methoxy-5-phenyl-1,4-benzothiazepine 1,1-dioxide;
3,3-Diethyl-2,3,4,5-tetrahydro-5-phenyl-1,4-benzothiazpin-4,8-diol 1,1-dioxide;
(RS)-3,3-Diethyl-2,3,4,5-tetrahydro-4-hydroxy-7,8-dimethoxy-5-phenyl-1,4-benzothiazepine 1,1-dioxide;
(+−)-Trans-3-butyl-8-ethoxy-3-ethyl-2,3,4,5-tetrahydro-5-phenyl-1,4-benzothiazepin-4-ol-1-dioxide;
(+−)-Trans-3-butyl-3-ethyl-2,3,4,5-tetrahydro-8-isopropoxy-5-phenyl-1.4-benzothiazepin-4-ol 1,1-dioxide;
(+−)-Trans-3-butyl-3-ethyl-2,3,4,5-tetrahydro-7,8,9-trimethoxy-5-phenyl-1,4-benzothiazepin-4-ol 1,1-dioxide;
(3R,5R)-3-butyl-3-ethyl-2,3,4,5-tetrahydro-5-phenyl-1,4-benzothiazpin-4,7,8-triol 1,1-dioxide;
(+−)-Trans-3-butyl-3-ethyl-2,3,4,5-tetrahydro-4,7,8-trimethoxy-5-phenyl-1,4-benzothiazepine 1,1-dioxide;
3,3-Diethyl-2,3,4,5-tetrahydro-5-phenyl-1,4-benzothiazepin-8-ol 1,1-dioxide;
3,3-Diethyl-2,3,4,5-tetrahydro-7-methoxy-5-phenyl-1,4-benzothiazepin-8-ol 1,1-dioxide;
3,3Dibutyl-2,3,4,5-tetrahydro-5-phenyl-1,4-benzothiazepin-8-ol 1,1-dioxide;
(+−)-Trans-3-Butyl-3-ethyl-2,3,4,5-tetrahydro-1,1-dioxo-5-phenyl-1,4-benzothiazepin-8-yl hydrogen sulfate; and
3,3-Diethyl-2,3,4,5-tetrahydro-1,1-dioxo-5-phenyl-1,4-benzothiazepin-8-yl hydrogen sulfate.

3. (3R,5R)-3-Butyl-3-ethyl-2,3,4,5-tetrahydro-7,8-dimethoxy-5-phenyl-1,4-benzothiazepine 1,1-dioxide, or a salt, solvate, or physiologically functional derivative thereof.

4. The compounds of claim 1 wherein R$^5$ and R$^8$ are both hydrogen; R$^6$ is C$_{1-4}$ alkyl optionally substituted by fluorine, C$_{1-4}$ alkoxy, halogen or hydroxy; and R$^7$ is C$_{1-4}$ alkoxy, halogen, hydroxy, or —S(O)$_n$R$^{15}$.

5. The compounds of claim 1 wherein R$^5$ and R$^8$ are both hydrogen; R$^6$ is methyl, methoxy, hydroxy, trifluoromethyl or chloro; and R$^7$ is methoxy, hydroxy, or —S(O)$_n$R$^{15}$.

6. The compounds of claim 1 wherein R$^5$ and R$^8$ are both hydrogen; R$^6$ is methoxy, hydroxy, or chloro; and R$^7$ is methoxy, hydroxy, or —S(O)$_n$R$^{15}$.

7. The compounds of claim 1 wherein R$^1$ is n-butyl; R$^2$ is ethyl; R$^3$, R$^5$, R$^8$, R$^9$, and R$^{10}$ are hydrogen; R$^6$ is methoxy, or hydroxy; and R$^7$ is methoxy, hydroxy, or —S(O)$_n$R$^{15}$.

8. (3R,5R)-3-Butyl-3-ethyl-2,3,4,5-tetrahydro-7-methoxy-5-phenyl-1,4-benzothiazepin-8-ol 1,1-dioxide, or a salt, solvate, or physiologically functional derivative thereof.

9. (+−)-Trans-3-butyl-3-ethyl-2,3,4,5-tetrahydro-5-phenyl-1,4-benzothiazepin-8-sulfonic acid 1,1-dioxide, or a salt, solvate, or physiologically functional derivative thereof.

10. A method of inhibiting the absorption of bile acids from the intestine of a mammal which comprises administering an effective bile acid absorption inhibiting amount of a compound of claim 1 to the mammal.

11. A method of reducing the blood plasma or serum concentrations of LDL and VLDL cholesterol in a mammal which comprises administering an effective cholesterol reducing amount of a compound of claim 5 to the mammal.

12. A method of reducing the concentrations of cholesterol and cholesterol ester in the blood plasma or serum of a mammal which comprises administering an effective cholesterol and cholesterol ester reducing amount of a compound of claim 1 to the mammal.

13. A method of increasing the fecal excretion of bile acids in a mammal which comprises administering an effective bile acid fecal excretion increasing amount of a compound of claim 1 to the mammal.

14. A method of reducing the incidence of coronary heart disease-related events in a mammal which comprises administering an effective coronary heart disease-related events reducing amount of a compound of claim 1 to the mammal.

15. A method of reducing the concentration of cholesterol in the blood plasma or serum of a mammal which comprises administering an effective cholesterol reducing amount of a compound of claim 1 to the mammal.

16. A method of treating a clinical condition in a mammal for which a bile acid uptake inhibitor is indicated which comprises, administering to a mammal an effective bile acid uptake inhibition amount of a compound of formula (IVa):

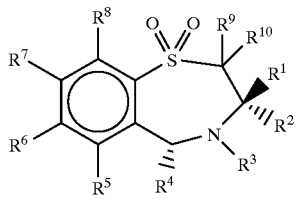

(IVa)

wherein
R$^1$ is a straight chained C$_{1-6}$ alkyl group;
R$^2$ is a straight chained C$_{1-6}$ alkyl group;
R$^3$ is hydrogen or a group OR$^{11}$ in which R$^{11}$ is hydrogen, optionally substituted C$_{1-6}$ alkyl or a C$_{1-6}$ alkylcarbonyl group;
R$^4$ is un-substituted phenyl;
R$^5$ is hydrogen;
R$^6$ and R$^8$ are independently selected from hydrogen, C$_{1-4}$ alkyl optionally substituted by fluorine, C$_{1-4}$ alkoxy, halogen, or hydroxy;
R$^7$ is selected from OR$^{15}$, S(O)$_n$R$^{15}$, OCOR$^{15}$, OCF$_3$, OCN, SCN, CHO, OCH$_2$OR$^{15}$, OCH=CHR$^{15}$, O(CH$_2$CH$_2$O)nR$^{15}$, O(CH$_2$)$_p$SO$_3$R$^{15}$, O(CH$_2$)$_p$NR$^{12}$R$^{13}$ and O(CH$_2$)$_p$N$^+$R$^{12}$R$^{13}$R$^{14}$ wherein p is an integer from 1-4, n is an integer from 0-3, and R$^{12}$, R$^{13}$, R$^{14}$, and R$^{15}$ are independently selected from hydrogen and optionally substituted C$_{1-6}$ alkyl;

R$^9$ and R$^{10}$ are the same or different and each is selected from hydrogen or C$_{1-6}$ alkyl; and salts, solvates and physiologically functional derivatives thereof.

17. The method of claim 16 wherein the compound of formula (IVa) is selected from:

(3R,5R)-3-Butyl-3-ethyl-2,3,4,5-tetrahydro-7,8-dimethoxy-5-phenyl-1,4-benzothiazepine 1,1-dioxide;

(3R,5R)-3-Butyl-3-ethyl-2,3,4,5-tetrahydro-7,8-dimethoxy-5-phenyl-1,4-benzothiazepin-4-ol 1,1-dioxide;

(+−)-Trans-3-butyl-3-ethyl-2,3,4,5-tetrahydro-7,8-dimethoxy-5-phenyl-1,4-benzothiazepine 1,1-dioxide;

(+−)-Trans-3-butyl-3-ethyl-2,3,4,5-tetrahydro-7,8-dimethoxy-5-phenyl-1,4,-benzothiazepin-4-ol 1,1-dioxide;

(3R,5R)-7-Bromo-3-butyl-3-ethyl-2,3,4,5-tetrahydro-8-methoxy-5-phenyl-1,4-benzothiazepine 1,1-dioxide;

(3R,5R)-7-Bromo-3-butyl-3-ethyl-2,3,4,5-tetrahydro-8-methoxy-5-phenyl-1,4-benzothiazepin-4-ol 1,1-dioxide;

(3R,5R)-3-Butyl-3-ethyl-2,3,4,5-tetrahydro-5-phenyl-1,4-benzothiazepine-7,8-diol 1,1-dioxide;

(3R,5R)-3-Butyl-3-ethyl-2,3,4,5-tetrahydro-8-methoxy-5-phenyl-1,4-benzothiazepin-7-ol 1,1-dioxide;

(3R,5R)-3-Butyl-3-ethyl-2,3,4,5-tetrahydro-7-methoxy-5-phenyl-1,4-benzothiazepin-8-ol 1,1-dioxide;

(+−)-Trans-3-butyl-3-ethyl-2,3,4,5-tetrahydro-8-methoxy-5-phenyl-1,4-benzothiazepine 1,1-dioxide;

(+−)-Trans-3-butyl-3-ethyl-2,3,4,5-tetrahydro-5-phenyl-1,4-benzothiazepin-8-ol 1,1-dioxide;

(+−)-Trans-3-butyl-3-ethyl-2,3,4,5-tetrahydro-5-phenyl-1,4-benzothiazepine-4,8-diol;

(+−)-Trans-3-butyl-3-ethyl-2,3,4,5-tetrahydro-5-phenyl-1,4-benzothiazepin-8-thiol 1,1-dioxide;

(+−)-Trans-3-butyl-3-ethyl-2,3,4,5-tetrahydro-5-phenyl-1,4-benzothiazepin-8-sulfonic acid 1,1-dioxide;

(+−)-Trans-3-butyl-3-ethyl-2,3,4,5-tetrahydro-8,9-dimethoxy-5-phenyl-1,4-benzothiazepine-1,1-dioxide;

(3R,5R)-3-butyl-7,8-diethoxy-2,3,4,5-tetrahydro-5-phenyl-1,4-benzothiazepine 1,1-dioxide;

(+−)-Trans-3-butyl-8-ethoxy-3-ethyl-2,3,4,5-tetrahydro-5-phenyl-1,4-benzothiazepine-1,1-dioxide;

(+−)-Trans-3-butyl-3-ethyl-2,3,4,5-tetrahydro-8-isopropoxy-5-phenyl-1,4-benzothiazepine 1,1-dioxide hydrochloride;

(+−)-Trans-3-butyl-3-ethyl-2,3,4,5-tetrahydro-5-phenyl-1,4-benzothiazepin-8-carbaldehyde-1,1-dioxide;

3,3-Diethyl-2,3,4,5-tetrahydro-7,8-dimethoxy-5-phenyl-1,4-benzothiazepine 1,1-dioxide;

3,3-Diethyl-2,3,4,5-tetrahydro-8-methoxy-5-phenyl-1,4-benzothiazepine 1,1-dioxide;

3,3-Diethyl-2,3,4,5-tetrahydro-5-phenyl-1,4-benzothiazpin-4,8-diol 1,1-dioxide;

(RS)-3,3-Diethyl-2,3,4,5-tetrahydro-4-hydroxy-7,8-dimethoxy-5-phenyl-1,4-benzothiazepine 1,1-dioxide;

(+−)-Trans-3-butyl-8-ethoxy-3-ethyl-2,3,4,5-tetrahydro-5-phenyl-1,4-benzothiazepin-4-ol-1,1-dioxide;

(+−)-Trans-3-butyl-3-ethyl-2,3,4,5-tetrahydro-8-isopropoxy-5-phenyl-1,4-benzothiazepin-4-ol 1,1-dioxide;

(+−)-Trans-3-butyl-3-ethyl-2,3,4,5-tetrahydro-7,8,9-trimethoxy-5-phenyl-1,4-benzothiazepin-4-ol 1,1-dioxide;

37

(3R,5R)-3-butyl-3-ethyl-2,3,4,5-tetrahydro-5-phenyl-1,4-benzothiazpin-4,7,8-triol 1,1-dioxide;
(+-)-Trans-3-butyl-3-ethyl-2,3,4,5-tetrahydro-4,7,8-trimethoxy-5-phenyl-1,4-benzothiazepine 1,1-dioxide;
3,3-Diethyl-2,3,4,5-tetrahydro-5-phenyl-1,4-benzothiazpin-8-ol 1,1-dioxide;
3,3-Diethyl-2,3,4,5-tetrahydro-7-methoxy-5-phenyl-1,4-benzothiazepin-8-ol 1,1-dioxide;
3,3Dibutyl-2,3,4,5-tetrahydro-5-phenyl-1,4-benzothiazepin-8-ol 1,1-dioxide;
(+-)-Trans-3-Butyl-3-ethyl-2,3,4,5-tetrahydro-1,1-dioxo-5-phenyl-1,4-benzothiazepin-8-yl hydrogen sulfate; and
3,3-Diethyl-2,3,4,5-tetrahydro-1,1-dioxo-5-phenyl-1,4-benzothiazepin-8-yl hydrogen sulfate.

18. The method of claim 17 wherein the compound is selected from:
   (3R,5R)-3-Butyl-3-ethyl-2,3,4,5-tetrad hydro-7,8-dimethoxy-5-phenyl-1,4-benzothiazepine 1,1-dioxide;
   (3R,5R)-3-Butyl-3-ethyl-2,3,4,5-tetrahydro-7-methoxy-5-phenyl-1,4-benzothiazepin-8-ol 1,1-dioxide;
   (+-)-Trans-3-butyl-3-ethyl-2,3,4,5-tetrahydro-5-phenyl-1,4-benzothiazepin-8-sulfonic acid 1,1-dioxide; or a salt, solvate, or physiologically functional derivative thereof.

19. A method of treating a hyperlipidemic condition in a mammal which comprises, administering to the mammal an effective hyperlipidemic treatment amount of a compound of formula (IVa):

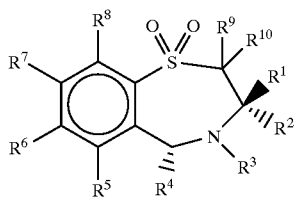

(IVa)

wherein
   $R^1$ is a straight chained $C_{1-6}$ alkyl group;
   $R^2$ is a straight chained $C_{1-6}$ alkyl group;
   $R^3$ is hydrogen or a group $OR^{11}$ in which $R^{11}$ is hydrogen, optionally substituted $C_{1-6}$ alkyl or a $C_{1-6}$ alkylcarbonyl group;
   $R^4$ is un-substituted phenyl;
   $R^5$ is hydrogen;
   $R^6$ and $R^8$ are independently selected from hydrogen, $C_{1-4}$ alkyl optionally substituted by fluorine, $C_{1-4}$ alkoxy, halogen, or hydroxy;
   $R^7$ is selected from $OR^{15}$, $S(O)_nR^{15}$, $OCOR^{15}$, $OCF_3$, OCN, SCN, CHO, $OCH_2OR^{15}$, $OCH=CHR^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein p is an integer from 1–4, n is an integer from 0–3, and $R^{12}$, $R^{13}$, $R^{14}$, and $R^{15}$ are independent selected from hydrogen and optionally substituted $C_{1-6}$ alkyl;
   $R^9$ and $R^{10}$ are the same or different and each is selected from hydrogen or $C_{1-6}$ alkyl; and salts, solvates and physiologically functional derivatives thereof.

20. The method of claim 19 wherein the compound of formula (IVa) is selected from:

38

(3R,5R)-3-Butyl-3-ethyl-2,3,4,5-tetrahydro-7,8-dimethoxy-5-phenyl-1,4-benzothiazepine 1,1-dioxide;
(3R,5R)-3-Butyl-3-ethyl-2,3,4,5-tetrahydro-7,8-dimethoxy-5-phenyl-1,4-benzothiazepin-4-ol 1,1-dioxide;
(+-)-Trans-3-butyl-3-ethyl-2,3,4,5-tetrahydro-7,8-dimethoxy-5-phenyl-1,4-benzothiazepine 1,1-dioxide;
(+-)-Trans-3-butyl-3-ethyl-2,3,4,5-tetrahydro-7,8-dimethoxy-5-phenyl-1,4,-benzothiazepin-4-ol 1,1-dioxide;
(3R,5R)-7-Bromo-3-butyl-3-ethyl-2,3,4,5-tetrahydro-8-methoxy-5-phenyl-1,4-benzothiazepine 1,1-dioxide;
(3R,5R)-7-Bromo-3-butyl-3-ethyl-2,3,4,5-tetrahydro-8-methoxy-5-phenyl-1,4-benzothiazepin-4-ol 1,1-dioxide;
(3R,5R)-3-Butyl-3-ethyl-2,3,4,5-tetrahydro-5-phenyl-1,4-benzothiazepine-7,8-diol 1,1-dioxide;
(3R,5R)-3-Butyl-3-ethyl-2,3,4,5-tetrahydro-8-methoxy-5-phenyl-1,4-benzothiazepin-7-ol 1,1-dioxide;
(3R,5R)-3-Butyl-3-ethyl-2,3,4,5-tetrahydro-7-methoxy-5-phenyl-1,4-benzothiazepin-8-ol 1,1-dioxide;
(+-)-Trans-3-butyl-3-ethyl-2,3,4,5-tetrahydro-8-methoxy-5-phenyl-1,4-benzothiazepine 1,1-dioxide;
(+-)-Trans-3-butyl-3-ethyl-2,3,4,5-tetrahydro-5-phenyl-1,4-benzothiazepin-8-ol 1,1-dioxide;
(+-)-Trans-3-butyl-3-ethyl-2,3,4,5-tetrahydro-5-phenyl-1,4-benzothiazepine-4,8-diol;
(+-)-Trans-3-butyl-3-ethyl-2,3,4,5-tetrahydro-5-phenyl-1,4-benzothiazepin-8-thiol 1,1-dioxide;
(+-)-Trans-3-butyl-3-ethyl-2,3,4,5-tetrahydro-5-phenyl-1,4-benzothiazepin-8-sulfonic acid 1,1-dioxide;
(+-)-Trans-3-butyl-3-ethyl-2,3,4,5-tetrahydro-8,9-dimethoxy-5-phenyl-1,4-benzothiazepine-1,1-dioxide;
(3R,5R)-3-butyl-7,8-diethoxy-2,3,4,5-tetrahydro-5-phenyl-1,4-benzothiazepine 1,1-dioxide;
(+-)-Trans-3-butyl-8-ethoxy-3-ethyl-2,3,4,5-tetrahydro-5-phenyl-1,4-benzothiazepine-1,1-dioxide;
(+-)-Trans-3-butyl-3-ethyl-2,3,4,5-tetrahydro-8-isopropoxy-5-phenyl-1,4-benzothiazepine 1,1-dioxide hydrochloride;
(+-)-Trans-3-butyl-3-ethyl-2,3,4,5-tetrahydro-5-phenyl-1,4-benzothiazepin-8-carbaldehyde-1,1-dioxide;
3,3-Diethyl-2,3,4,5-tetrahydro-7,8-dimethoxy-5-phenyl-1,4-benzothiazepine 1,1-dioxide;
3,3-Diethyl-2,3,4,5-tetrahydro-8-methoxy-5-phenyl-1,4-benzothiazepine 1,1-dioxide;
3,3-Diethyl-2,3,4,5-tetrahydro-5-phenyl-1,4-benzothiazpin-4,8-diol 1,1-dioxide;
(RS)-3,3-Diethyl-2,3,4,5-tetrahydro-4-hydroxy-7,8-dimethoxy-5-phenyl-1,4-benzothiazepine 1,1-dioxide;
(+-)-Trans-3-butyl-8-ethoxy-3-ethyl-2,3,4,5-tetrahydro-5-phenyl-1,4-benzothiazepin-4-ol-1,1-dioxide;
(+-)-Trans-3-butyl-3-ethyl-2,3,4,5-tetrahydro-8-isopropoxy-5-phenyl-1,4-benzothiazepin-4-ol-1,1-dioxide-;
(+-)-Trans-3-butyl-3-ethyl-2,3,4,5-tetrahydro-7,8,9-trimethoxy-5-phenyl-1,4-benzothiazepin-4-ol 1,1-dioxide;
(3R,5R)-3-butyl-3-ethyl-2,3,4,5-tetrahydro-5-phenyl-1,4-benzothiazpin-4,7,8-triol 1,1dioxide;
(+-)-Trans-3-butyl-3-ethyl-2,3,4,5-tetrahydro-4,7,8-trimethoxy-5-phenyl-1,4-benzothiazepine 1,1-dioxide;

3,3-Diethyl-2,3,4,5-tetrahydro-5-phenyl-1,4-benzothiazepin-8-ol 1,1-dioxide;

3,3-Diethyl-2,3,4,5-tetrahydro-7-methoxy-5-phenyl-1,4-benzothiazepin-8-ol 1,1-dioxide;

3,3Dibutyl-2,3,4,5-tetrahydro-5-phenyl-1,4-benzothiazepin-8-ol 1,1-dioxide;

(+−)-Trans-3-Butyl-3-ethyl-2,3,4,5-tetrahydro-1,1-dioxo-5-phenyl-1,4-benzothiazepin-8-yl hydrogen sulfate; and 3,3-Diethyl-2,3,4,5-tetrahydro-1,1-dioxo-5-phenyl-1,4-benzothiazepin-8-yl hydrogen sulfate.

21. The method of claim 20 wherein the compound is selected from:

(3R,5R)-3-Butyl-3-ethyl-2,3,4,5-tetradhydro-7,8-dimethoxy-5-phenyl-1,4-benzothiazepine 1,1-dioxide;

(3R,5R)-3-Butyl-3-ethyl-2,3,4,5-tetrahydro-7-methoxy-5-phenyl-1,4-benzothiazepin-8-ol 1,1-dioxide;

(+−)-Trans-3-butyl-3-ethyl-2,3,4,5-tetrahydro-5-phenyl-1,4-benzothiazepin-8-sulfonic acid 1,1-dioxide; or a salt, solvate, or physiologically functional derivative thereof.

22. The method of claim 19 wherein the hyperlipidemic condition is atherosclerosis.

23. A pharmaceutical composition comprising a compound of formula (IVa):

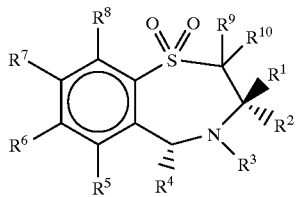

(IVa)

wherein $R^1$ is a straight chained $C_{1-6}$ alkyl group;

$R^2$ is a straight chained $C_{1-6}$ alkyl group;

$R^3$ is hydrogen or a group $OR^{11}$ in which $R^{11}$ is hydrogen, optionally substituted $C_{1-6}$ alkyl or a $C_{1-6}$ alkylcarbonyl group;

$R^4$ is un-substituted phenyl;

$R^5$ is hydrogen;

$R^6$ and $R^8$ are independently selected from hydrogen, $C_{1-4}$ alkyl optionally substituted by fluorine, $C_{1-4}$ alkoxy, halogen, or hydroxy;

$R^7$ is selected from $OR^{15}$, $S(O)_nR^{15}$, $OCOR^{15}$, $OCF_3$, OCN, SCN, CHO, $OCH_2OR^{15}$, $OCH=CHR^{15}$, $O(CH_2CH_2O)nR^{15}$, $O(CH_2)_pSO_3R^{15}$, $O(CH_2)_pNR^{12}R^{13}$ and $O(CH_2)_pN^+R^{12}R^{13}R^{14}$ wherein p is an integer from 1–4, n is an integer from 0–3, and $R^{12}$, $R^{13}$, $R^{14}$, and $R^{15}$ are independently selected from hydrogen and optionally substituted $C_{1-6}$ alkyl;

$R^9$ and $R^{10}$ are the same or different and each is selected from hydrogen or $C_{1-6}$ alkyl; and salts, solvates and physiologically functional derivatives thereof, at least one pharmaceutically acceptable carrier, and optionally one or more other physiologically active agents.

24. The pharmaceutical composition of claim 23 wherein the compound of formula (IVa) is selected from:

(3R,5R)-3-Butyl-3-ethyl-2,3,4,5-tetrahydro-7,8-dimethoxy-5-phenyl-1,4-benzothiazepine 1,1-dioxide;

(3R,5R)-3-Butyl-3-ethyl-2,3,4,5-tetrahydro-7,8-dimethoxy-5-phenyl-1,4-benzothiazepin-4-ol 1,1-dioxide;

(+−)-Trans-3-butyl-3-ethyl-2,3,4,5-tetrahydro-7,8-dimethoxy-5-phenyl-1,4-benzothiazepine 1,1-dioxide;

(+−)-Trans-3-butyl-3-ethyl-2,3,4,5-tetrahydro-7,8-dimethoxy-5-phenyl-1,4-benzothiazepin-4-ol 1,1-dioxide;

(3R,5R)-7-Bromo-3-butyl-3-ethyl-2,3,4,5-tetrahydro-8-methoxy-5-phenyl-1,4-berizothiazepine 1,1-dioxide;

(3R,5R)-7-Bromo-3-butyl-3-ethyl-2,3,4,5-tetrahydro-8-methoxy-5-phenyl-1,4-benzothiazepin-4-ol 1,1-dioxide;

(3R,5R)-3-Butyl-3-ethyl-2,3,4,5-tetrahydro-5-phenyl-1,4-benzothiazepine-7,8-diol 1,1 dioxide;

(3R,5R)-3-Butyl-3-ethyl-2,3,4,5-tetrahydro-8-methoxy-5-phenyl-1,4-benzothiazepin-7-ol 1,1-dioxide;

(3R,5R)-3-Butyl-3-ethyl-2,3,4,5-tetrahydro-7-methoxy-5-phenyl-1,4-benzothiazepin-8-ol 1,1-dioxide;

(+−)-Trans-3-butyl-3-ethyl-2,3,4,5-tetrahydro-8-methoxy-5-phenyl-1,4-benzothiazepine 1,1-dioxide;

(+−)-Trans-3-butyl-3-ethyl-2,3,4,5-tetrahydro-5-phenyl-1,4-benzothiazepin-8-ol 1,1-dioxide;

(+−)-Trans-3-butyl-3-ethyl-2,3,4,5-tetrahydro-5-phenyl-1,4-benzothiazepine-4,8-diol;

(+−)-Trans-3-butyl-3-ethyl-2,3,4,5-tetrahydro-5-phenyl-1,4-benzothiazepin-8-thiol 1,1-dioxide;

(+−)-Trans-3-butyl-3-ethyl-2,3,4,5-tetrahydro-5-phenyl-1,4-benzothiazepin-8-sulfonic acid 1,1-dioxide;

(+−)-Trans-3-butyl-3-ethyl-2,3,4,5-tetrahydro-8,9-dimethoxy-5-phenyl-1,4-benzothiazepine-1,1-dioxide;

(3R,5R)-3-butyl-7,8-diethoxy-2,3,4,5-tetrahydro-5-phenyt-1,4-benzothiazepine 1,1-dioxide;

(+−)-Trans-3-butyl-8-ethoxy-3-ethyl-2,3,4,5-tetrahydro-5-phenyl-1,4-benzothiazepine-1,1-dioxide;

(+−)-Trans-3-butyl-3-ethyl-2,3,4,5-tetrahydro-8-isopropoxy-5-phenyl-1,4-benzothiazepine 1,1-dioxide hydrochloride;

(+−)-Trans-3-butyl-3-ethyl-2,3,4,5-tetrahydro-5-phenyl-1,4-benzothiazepin-8-carbaldehyde-1,1-dioxide;

3,3-Diethyl-2,3,4,5-tetrahydro-7,8-dimethoxy-5-phenyl-1,4-benzothiazepine 1,1-dioxide;

3,3-Diethyl-2,3,4,5-tetrahydro-8-methoxy-5-phenyl-1,4-benzothiazepine 1,1-dioxide;

3,3-Diethyl-2,3,4,5-tetrahydro-5-phenyl-1,4-benzothiazpin-4,8-diol 1,1-dioxide;

(RS)-3,3-Diethyl-2,3,4,5-tetrahydro-4-hydroxy-7,8-dimethoxy-5-phenyl-1,4-benzothiazepine 1,1-dioxide;

(+−)-Trans-3-butyl-8-ethoxy-3-ethyl-2,3,4,5-tetrahydro-5-phenyl-1,4-benzothiazepin-4-ol-1,1-dioxide;

(+−)-Trans-3-butyl-3-ethyl-2,3,4,5-tetrahydro-8-isopropoxy-5-phenyl-1,4-benzothiazepin-4-ol 1,1-dioxide;

(+−)-Trans-3-butyl-3-ethyl-2,3,4,5-tetrahydro-7,8,9-trimethoxy-5-phenyl-1,4-benzothiazepin-4-ol 1,1-dioxide;

(3R,5R)-3-butyl-3-ethyl-2,3,4,5-tetrahydro-5-phenyl-1,4-benzothiazpin-4,7,8-triol 1,1-dioxide;

(+−)-Trans-3-butyl-3-ethyl-2,3,4,5-tetrahydro-4,7,8-trimethoxy-5-phenyl-1,4-benzothiazepine 1,1-dioxide;

3,3-Diethyl-2,3,4,5-tetrahydro-5-phenyl-1,4-benzothiazepin-8-ol 1,1-dioxide;

3,3-Diethyl-2,3,4,5-tetrahydro-7-methoxy-5-phenyl-1,4-benzothiazepin-8-ol 1,1-dioxide;

3,3-Dibutyl-2,3,4,5-tetrahydro-5-phenyl-1,4-benzothiazepin-8-ol 1,1-dioxide;

(+−)-Trans-3-Butyl-3-ethyl-2,3,4,5-tetrahydro-1,1-dioxo-5-phenyl-1,4-benzothiazepin-8-yl hydrogen sulfate; and 3,3-Diethyl-2,3,4,5-tetrahydro-1,1-dioxo-5-phenyl-1,4-benzothiazepin-8-yl hydrogen sulfate.

25. The pharmaceutical composition of claim 24 wherein the compound is selected from:

(3R,5R)-3-Butyl-3-ethyl-2,3,4,5-tetradhydro-7,8-dimethoxy-5-phenyl-1,4-benzothiazepine 1,1-dioxide;

(3R,5R)-3-Butyl-3-ethyl-2,3,4,5-tetrahydro-7-methoxy-5-phenyl-1,4-benzothiazepin-8-ol 1,1-dioxide;

(+−)-Trans-3-butyl-3-ethyl-2,3,4,5-tetrahydro-5-phenyl-1,4-benzothiazepin-8-sulfonic acid 1,1-dioxide; or a salt, solvate, or physiologically functional derivative thereof.

26. The pharmaceutical composition of claim 23 which is an enteric coated tablet or capsule.

27. The pharmaceutical composition of claim 24 which is an enteric coated tablet or capsule.

28. The pharmaceutical composition of claim 25 which is an enteric coated tablet or capsule.

* * * * *

UNITED STATES PATENT AND TRADEMARK OFFICE
CERTIFICATE OF CORRECTION

PATENT NO. : 5,910,494
DATED : June 8, 1999
INVENTOR(S) : Lawrence Edward Brieaddy It is certified that error appears in the above-identified patent and that said Letters Patent are hereby corrected as shown below:

Column 35, line 16, change "5" to --1--;

Column 37, line 9, change "3,3 Dibutyl-" to --3,3-Dibutyl-";
       line 19, change "-2,3,4,5-tetrad hydro-7,8-" to -- -2,3,4,5-tetrahydro-7,8- --;

Column 38, line 64, change "1,1dioxide" to --1,1-dioxide--;

Column 40, line 10, change "-berizothiazepine" to -- -benzothiazepine--; and
       line 35, change "5-phenyt-" to --5-phenyl- --.

Signed and Sealed this

Fourteenth Day of December, 1999

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,910,494
DATED : June 8, 1999
INVENTOR(S) : Lawrence Edward Brieaddy It is certified that error appears in the above-identified patent and that said Letters Patent is hereby corrected as shown below:

Col. 1, line 1: please correct the priority information to include -- U.S. Application Serial No. 08/288,527, filed August 10, 1994, now abandoned--,.

Signed and Sealed this

Thirty-first Day of October, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 5,910,494
DATED : June 8, 1999
INVENTOR(S) : Lawrence E. Brieaddy

It is certified that error appears in the above-identified patent and that said Letters Patent is hereby corrected as shown below:

Column 14,
Line 35, delete "(h) 2-Hydroxy-4,5-dimethoxybenzaldehyde" and insert therefor
-- (h) 2-Hydroxy-4,5-dimethoxybenzophenone --.

Signed and Sealed this

Sixth Day of August, 2002

Attest:

Attesting Officer

JAMES E. ROGAN
*Director of the United States Patent and Trademark Office*